(12) United States Patent
Parker et al.

(10) Patent No.: US 11,951,149 B2
(45) Date of Patent: Apr. 9, 2024

(54) INTRANASAL VASOPRESSIN TREATMENT OF SOCIAL DEFICITS IN AUTISM

(71) Applicant: The Board of Trustees of the Leland Stanford Junior University, Stanford, CA (US)

(72) Inventors: Karen J. Parker, Stanford, CA (US); Dean S. Carson, San Francisco, CA (US); Antonio Y. Hardan, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 99 days.

(21) Appl. No.: 17/252,186

(22) PCT Filed: Jul. 10, 2019

(86) PCT No.: PCT/US2019/041250
§ 371 (c)(1),
(2) Date: Dec. 14, 2020

(87) PCT Pub. No.: WO2020/014394
PCT Pub. Date: Jan. 16, 2020

(65) Prior Publication Data
US 2021/0260152 A1    Aug. 26, 2021

Related U.S. Application Data

(60) Provisional application No. 62/696,234, filed on Jul. 10, 2018.

(51) Int. Cl.
*A61K 38/095* (2019.01)
*A61K 9/00* (2006.01)
*A61K 38/09* (2006.01)
*G01N 33/74* (2006.01)

(52) U.S. Cl.
CPC .......... *A61K 38/095* (2019.01); *A61K 9/0043* (2013.01); *G01N 33/74* (2013.01); *G01N 2333/575* (2013.01)

(58) Field of Classification Search
CPC .... A61K 38/095; A61K 9/0043; A61K 38/09; A61K 9/00; C01N 33/74; G01N 33/74
See application file for complete search history.

(56) References Cited

U.S. PATENT DOCUMENTS

| | | |
|---|---|---|
| 2011/0183904 A1 | 7/2011 | Jacobson et al. |
| 2014/0073562 A1 | 3/2014 | Djupesland et al. |
| 2015/0111946 A1 | 4/2015 | Harmon et al. |
| 2016/0000945 A1 | 1/2016 | Nedergaard et al. |
| 2018/0085423 A1 | 3/2018 | Zeltser et al. |

OTHER PUBLICATIONS

Busner et al., "Impressions Scale: Applying a Research Tool in Clinical Practice," Psychiatry, 2007, 28-37. (Year: 2007).*
Parker et al., "Intranasal Vasopressin Treatment Improves Social Abilities in Children with Autism," International Society for Autism Research, May 11, 2017, pp. 1-3. (Year: 2017).*
Carson et al. (2015) "Arginine Vasopressin Is a Blood-Based Biomarker of Social Functioning in Children with Autism," PLoS One, vol. 10, No. 7, pp. 1-14.
Galbusera et al. (2016) "Intranasal Oxytocin and Vasopressin Modulate Divergent Brainwide Functional Substrates," Neuropsychopharmacology, vol. 42, Iss. 7, pp. 1420-1434.
Treschan et al. (2006) "The Vasopressin System: physiology and clinical strategies," Anesthesiology, vol. 105, No. 3, pp. 599-612.

* cited by examiner

*Primary Examiner* — Julie Ha
(74) *Attorney, Agent, or Firm* — Pamela J. Sherwood; Bozicevic, Field and Francis LLP (57) ABSTRACT

Provided herein are methods for treating, reducing and/or ameliorating symptoms of autism spectrum disorder (ASD) in a subject, where at least one measure of social impairment, anxiety, or repetitive behaviors is treated and/or ameliorated. Aspects include intranasally administering arginine vasopressin (AVP), or an analog of vasopressin, to a subject (e.g., a child between 6 and 12 years of age and having endogenous pre-treatment levels between about 0.045 and about 4.028 pg/mL, where the mean was 1.324 pg/mL). In children having high pre-treatment blood levels of AVP (e.g., about 25% or more above the mean pre-treatment AVP blood levels of the treatment group; or having pre-treatment blood vasopressin levels greater than 1.324 pg/mL), the treatment was enhanced. Because no difference in pre-treatment blood AVP levels was observed between control and ASD subjects, it was surprising that AVP treatment was more effective in subjects having high pre-treatment AVP levels.

8 Claims, 2 Drawing Sheets

Specification includes a Sequence Listing.

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Synthetic sequence

<400> SEQUENCE: 1
ctgaacatcc cgaggaactg                                                       20

<210> SEQ ID NO 2
<211> LENGTH: 20
<212> TYPE: DNA
<213> ORGANISM: Artificial Sequence
<220> FEATURE:
<223> OTHER INFORMATION: Synthetic sequence

<400> SEQUENCE: 2
ctctgagcca ctgcaaatga                                                       20

<210> SEQ ID NO 3
<211> LENGTH: 22
<212> TYPE: DNA
<213> ORGANISM: Artificial Sequence
<220> FEATURE:
<223> OTHER INFORMATION: Synthetic sequence

<400> SEQUENCE: 3
cttttgtgat cgtgacggct ta                                                    22

<210> SEQ ID NO 4
<211> LENGTH: 22
<212> TYPE: DNA
<213> ORGANISM: Artificial Sequence
<220> FEATURE:
<223> OTHER INFORMATION: Synthetic sequence

<400> SEQUENCE: 4
tgatggtagg gttttccgat tc                                                    22

<210> SEQ ID NO 5
```

```
<211> LENGTH: 21
<212> TYPE: DNA
<213> ORGANISM: Artificial Sequence
<220> FEATURE:
<223> OTHER INFORMATION: Synthetic sequence

<400> SEQUENCE: 5
ggacaggact gaacgtcttg c                                              21

<210> SEQ ID NO 6
<211> LENGTH: 20
<212> TYPE: DNA
<213> ORGANISM: Artificial Sequence
<220> FEATURE:
<223> OTHER INFORMATION: Synthetic sequence

<400> SEQUENCE: 6
atagcccccc ttgagcacac                                                20

<210> SEQ ID NO 7
<211> LENGTH: 20
<212> TYPE: DNA
<213> ORGANISM: Artificial Sequence
<220> FEATURE:
<223> OTHER INFORMATION: Synthetic sequence

<400> SEQUENCE: 7
gctgctcata agactcggcc                                                20

<210> SEQ ID NO 8
<211> LENGTH: 20
<212> TYPE: DNA
<213> ORGANISM: Artificial Sequence
<220> FEATURE:
<223> OTHER INFORMATION: Synthetic sequence

<400> SEQUENCE: 8
gtcacccaag tcccgtccta                                                20
```

INTRANASAL VASOPRESSIN TREATMENT OF SOCIAL DEFICITS IN AUTISM

CROSS REFERENCE TO RELATED APPLICATIONS

This application claims the priority of U.S. Provisional Appl. Ser. No. 62/696,234, filed Jul. 10, 2018, the entire disclosure of which is incorporated herein by reference in its entirety.

STATEMENT OF GOVERNMENT SUPPORT

This invention was made with Government support under contract MH100387 awarded by the National Institutes of Health. The Government has certain rights in the invention.

INTRODUCTION

Autism spectrum disorder (ASD) is a neurodevelopmental disorder characterized by social impairments (e.g., diminished eye gaze, abnormal face and emotion processing, impaired social judgment) and the presence of restricted, repetitive behaviors (1). Although several medications are approved for the treatment of ASD (i.e., the antipsychotics risperidone and aripiprazole), they have negative side-effects (e.g., lethargy; weight gain), target only associated behaviors (e.g., irritability), and are ineffective in ameliorating ASD's core social features. Research that identifies the underlying biology of social impairments and tests medications that directly target these pathways is therefore urgently needed (2).

SUMMARY

In some aspects, disclosed herein is a method of treating/ameliorating autism spectrum disorder (ASD) in a subject diagnosed with ASD, comprising administering intranasal arginine vasopressin (AVP), or an analog of vasopressin, to a subject having high endogenous pre-treatment blood levels of vasopressin (e.g., (a) greater than about 25% or more above the mean/normal pre-treatment vasopressin blood levels of the treatment group, or of a control subject or group of subjects (diagnosed or not diagnosed with ASD), and/or (b) ranging between 0.01 and 6.5 pg/mL, inclusive, endogenous pre-treatment vasopressin blood levels, whereby at least one measure of ASD-associated social impairment, anxiety, or repetitive behavior is treated and/or ameliorated. In some embodiments, the whole range of subjects responded to intranasal AVP treatment, and the surprising observation was that the response to the treatment was greater for those patients at the higher (above the mean) pre-treatment AVP levels.

As used herein, "mean pre-treatment endogenous vasopressin level," "mean/normal pre-treatment vasopressin level," and the like, refer to the calculated average value of the range of AVP levels in a bodily fluid such as blood before treatment with AVP or an analog thereof.

In some embodiments, no difference in pre-treatment blood AVP levels is observed between control and ASD subjects. However, a very surprising result was that, contrary to previous reports, intranasal delivery of AVP allowed all children diagnosed with ASD to perform better on the social cognition tests than those on placebo. That is to say, regardless of blood vasopressin level, these children on AVP performed better on the two social cognition tasks than those on placebo (while having no change in their baseline concomitant medications) suggesting that children with a wide range of pre-treatment vasopressin blood levels are treatable with AVP. Furthermore, it was unexpectedly observed that AVP treatment was more effective in subjects having high pre-treatment vasopressin levels (above the mean pre-treatment AVP blood level). Thus, in the present study, pre-treatment blood levels of vasopressin were predictive of the efficacy of response, as it was observed that when children with ASD who had high pre-treatment vasopressin levels were treated with intranasal AVP, they performed better on the social cognition tests than those children with ASD having low pre-treatment blood vasopressin levels. Furthermore, the results presented herein may be used to identify an ASD patient population in which the intranasal AVP treatment will be most effective, or may be used at a lower dose.

In some embodiments, "high" levels, with respect to endogenous AVP, means that the pre-treatment levels of AVP in the blood (or other bodily fluid) are above the mean/average of the mean calculated from the range of pre-treatment endogenous levels.

In some embodiments, the endogenous pre-treatment blood vasopressin level in the subject is greater than ($\geq$) about 0.025 pg/mL, or $\geq$about 0.03 pg/mL, or $\geq$about 0.04 pg/mL, or $\geq$about 0.05 pg/mL, or $\geq$about 0.1 pg/mL, or $\geq$about 0.25 pg/mL, or $\geq$about 0.5 pg/mL, or $\geq$about 1.0 pg/mL, or $\geq$about 2.0 pg/mL, or $\geq$about 3.0 pg/mL, or $\geq$about 4.0 pg/mL. In some embodiments, the range of endogenous pre-treatment blood vasopressin levels in the subject is between about 0.04 and about 4.0 pg/mL. In some embodiments, the range of endogenous pre-treatment blood vasopressin levels in the subject is between about 0.025 pg/mL and about 6.0 pg/mL, and the mean pre-treatment endogenous blood vasopressin level of this range is approximately 3.01 pg/mL. In some embodiments, the range of endogenous pre-treatment blood vasopressin levels in the subject is or between about 0.1 and about 5 pg/mL, and the mean pre-treatment endogenous blood vasopressin level of this range is approximately 2.55 pg/mL. In some embodiments, the range of endogenous pre-treatment blood vasopressin levels is between about 0.05 and about 3.5 pg/mL, and the mean pre-treatment endogenous blood vasopressin level of this range is approximately 1.775 pg/mL. In some embodiments, the range of endogenous pre-treatment blood vasopressin levels in the subject is greater than about 0.04 pg/mL. and less than about 4.5 pg/mL, and the mean pre-treatment endogenous blood vasopressin level of this range is approximately 2.27 pg/mL. In some embodiments, the subject is a child under age 18, and the range of endogenous pre-treatment levels is between 0.045 and 4.028 pg/mL, and the mean pre-treatment endogenous blood vasopressin level of this range is approximately 2.037 pg/mL.

In some embodiments, the subject is a child between 6 and 12 years of age, and the range of endogenous pre-treatment levels is between about 0.04 and about 4.0 pg/mL. In some embodiments, the range of endogenous pre-treatment levels is between 0.045 and 4.028 pg/mL, and the mean pre-treatment endogenous blood vasopressin level is 1.324 pg/mL, and thus, a "high" level of pre-treatment blood vasopressin levels in the subject is greater than 1.324 pg/mL. In some embodiments, a "high pre-treatment blood level of vasopressin" is 10% above the mean of the treatment group or of a control group. In some embodiments, a "high pre-treatment blood level of vasopressin" is 20% above the mean of the treatment group or of a control group. In some embodiments, a "high pre-treatment blood level of vasopressin" is 25% above the mean of the treatment group or of a control group. In some embodiments, a "high pre-treatment blood level of vasopressin" is 50% above the mean of the treatment group or of a control group. In some embodiments, a "high pre-treatment blood level of vasopressin" is 1.59 pg/mL. In some embodiments, a "high pre-treatment blood level of vasopressin" is 1.456 pg/mL. In some embodiments, a "high pre-treatment blood level of vasopressin" is 1.655 pg/mL. In some embodiments, a "high pre-treatment blood level of vasopressin" is 1.986 pg/mL. In some embodiments, a "high pre-treatment blood level of vasopressin" is 2.04 pg/mL. In some embodiments, a "high pre-treatment blood level of vasopressin" is 2.5 pg/mL.

In some embodiments of the method, the measurement of social impairment, anxiety, and/or repetitive behaviors is determined based on a scale selected from the Social Responsiveness Scale (SRS), as well as two subscales of the SRS: the Social Communication and Interaction (SCI) subscale and the restricted interests and repetitive behavior (RRB) subscale; the Clinical Global Impression-Improvement (CGI-I) scale; the Reading the Mind in the Eyes Test (RMET); the Facial Emotion Recognition Test (FERT); Spence Children's Anxiety Scale (SCAS); and the Repetitive Behaviors Scale-Revised (RBS-R).

In some embodiments of the method, the pre-treatment blood level of AVP of the subject (with or without ASD) is between 0.045 and 4.028 pg/mL. In some embodiments, the endogenous pre-treatment blood level of AVP of the subject is between 0.1 and 5.0 pg/mL. In some embodiments, the method treats social impairment and the social impairment is a simple social perceptual ability. In some embodiments, the method treats social impairment and the social impairment is a simple social perceptual ability. In some embodiments, the method treats social impairment and the social impairment is a complex social functioning ability. In some embodiments, the method treats anxiety associated with ASD. In some embodiments, the repetitive behavior manifests in the subject as a self-injurious behavior. In some embodiments, the method treats a restricted repetitive behavior.

In some embodiments of the method, the subject is a child. In some embodiments, the subject is 18 years of age or younger. In some embodiments, the subject is a child between 6 and 12 years of age. In some embodiments of the method, the subject is administered intranasal AVP twice daily. In some embodiments, the subject is administered up to 16 IU AVP twice daily. In some embodiments, the subject is between 6 and 9.5 years of age. In some embodiments, the subject is administered up to 16 IU AVP twice daily. In some embodiments, the subject is between 6 and 9.5 years of age and is administered intranasal AVP at a dose of about 12 IU twice daily. In some embodiments, the subject is between 9.6 and 13 years of age and is administered intranasal AVP at a dose of about 16 IU twice daily.

In some aspects, the subjects are stratified a priori on the basis of pre-treatment vasopressin blood levels, to identify a subset of subjects/patients in which administration of intranasal AVP is most effective in treating social and behavioral deficits. In some aspects, the subjects are stratified a priori on the basis of pre-treatment vasopressin blood levels, to identify a subset of subjects/patients in which a lower or higher dose of intranasal AVP is most effective for treating social and behavioral deficits. In some aspects, disclosed herein is a method of stratifying a population of pediatric subjects diagnosed with ASD into groups of subjects that are candidates for different effective dosage regimens, comprising measuring pre-treatment blood concentration of endogenous vasopressin in the population; and (i) assigning subjects having a pre-treatment endogenous vasopressin blood concentration of at least 0.045 pg/mL or more to a group to which a regimen of intranasally administered AVP begins at a lower effective dose, and optionally increases to a higher dose. In some embodiments, the population of pediatric subjects having ASD is stratified into groups of subjects that are candidates for different effective dosage regimens; and/or (ii) assigning subjects having a pre-treatment endogenous vasopressin blood concentration of between about 0.04 pg/mL and about 2.5 pg/mL to a treatment group to which a regimen of intranasally administered AVP may be effective at a low dose.

In some embodiments, the method of stratifying further comprises assigning genetically male subjects and genetically female subjects into separate subgroups.

In some aspects, disclosed herein is the use of a measure of the concentration of endogenous vasopressin in a bodily fluid selected from blood, serum, plasma, sputum, urine, and cerebrospinal fluid (CSF), to determine an effective dose of intranasally administered AVP or an analog thereof. In some aspects, disclosed herein is the use of a measure of the concentration of endogenous vasopressin in a bodily fluid selected from blood, serum, plasma, sputum, urine, and CSF, to identify a subgroup within a pediatric population as treatable with low-dose intranasally administered AVP or an analog thereof, wherein the subgroup comprises individuals within the group having "high" levels of endogenous vasopressin as compared to subjects having "normal" or "low" concentrations.

In some embodiments, the whole range of subjects responded to intranasal AVP treatment, and the surprising observation was that the response to the treatment was greater for those patients at the higher (above the mean) pre-treatment AVP levels.

BRIEF DESCRIPTION OF THE FIGURES

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DEFINITIONS

The terms "treatment," "treating," "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom(s) but has not yet been diagnosed as having it; (b) inhibiting the disease and/or symptom(s), i.e., arresting development of a disease and/or the associated symptoms; or (c) relieving the disease and the associated symptom(s), i.e., causing regression of the disease and/or symptom(s). Those in need of treatment can include those already afflicted (e.g., those patients/subjects having been diagnosed with ASD) as well as those in which prevention is desired (e.g., those with increased susceptibility or a genetic predisposition to ASD; those exhibiting symptoms of ASD; those suspected of having ASD; etc.).

As used herein, the terms "recipient," "individual," "subject," "host," and "patient" are used interchangeably herein and refer to any human subject for whom treatment, or therapy is desired.

The human posterior pituitary gland (neurohypophysis) secretes two neuropeptide hormones: oxytocin and vasopressin. These hormones are synthesized by the magnocellular neurons located in the supraoptic and paraventricular nuclei of the hypothalamus and are secreted out into the circulation through the posterior pituitary; thus, they act in an endocrine fashion at a distance from their site of synthesis, but also are released as neurotransmitters in the brain through distributed neural pathways. Without being limited by theory, it is herein suggested that the inhaled intranasal vasopressin is able to more directly access the brain and bind to receptors in the brain.

Oxytocin neurons make other peptides as well, including corticotropin-releasing hormone and dynorphin, for example, that act locally. Vasopressin is synthesized as a peptide prohormone and is converted to AVP. Vasopressins (VPs) are a mammalian family of nonapeptides composed of an intramolecular ring structure flanked by two cysteine residues (which form a disulfide bond) and a C-terminal extension with a basic amino acid residue at position 8. Vasopressin is also known as antidiuretic hormone (ADH), arginine vasopressin (AVP), 8-arginine vasopressin, [Arg8]-vasopressin, 8-L-argininevasopressin, Argipressin, beta-Hypophamine, Vasostrict®, Pressyn Ar, and Pitressin). The structure of exogenous vasopressin, commercially available as a sterile solution of synthetic vasopressin, is shown below.

As used herein, the phrase "vasopressin analog" can include: 1-deamino-8-D-arginine-vasopressin (also known as Desmopressin (dDAVP), desmopressin acetate, MINRIN®, 1-acetyl-8-lysine-vasopressin, DIAPID™ 8-L-Lysine vasopressin, Lysipressin, LYPRESSIN™, Lys-vasopressin, 3-(Phenylalanine)-8-lysine oxytocin) and Terlipressin (triglycyl-lysine vasopressin).

Terlipressin (triglycyl-lysine vasopressin) is a long-acting vasopressin analog wherein Lysine (Lys) is substituted for Arginine (Arg) at position 8; its structure is shown below:

The N-triglycyl residue in Terlipressin shown above is cleaved by endothelial peptidases, releasing the active lysine-vasopressin.

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks) after the administration of a second therapeutic agent.

The term "sample" as used herein relates to a material or mixture of materials, typically, although not necessarily, in fluid, i.e., aqueous, form, containing one or more components of interest. Samples may be derived from a variety of sources such as from a biological sample or solid, such as tissue or bodily fluid isolated from an individual, including but not limited to, for example, blood, serum, plasma, blood cells, saliva, sputum, tears, milk, urine, cerebrospinal fluid (CSF), semen, lymph fluid, the external sections of the skin, respiratory, intestinal, and genitourinary tracts, putatively virally infected cells, tumors, and organs. In certain embodiments of the method, the sample includes a cell. In some instances of the method, the cell is in vitro. In some instances of the method, the cell is in vivo.

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The terms "polynucleotide" and "nucleic acid" should be understood to include, as applicable to the embodiment being described, single-stranded (such as sense or antisense) and double-stranded polynucleotides.

The terms "polypeptide," "peptide," and "protein", are used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like. The term "polypeptide" includes lipoproteins, glycoproteins, and the like.

A "host cell," as used herein, denotes an in vivo or in vitro eukaryotic cell, or a cell from a multicellular organism (e.g., a cell line) cultured as a unicellular entity, which eukaryotic cells can be, or have been, used as recipients for a nucleic acid (e.g., an expression vector), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector, a guide RNA, a donor DNA template, and the like. For example, a subject eukaryotic host cell is a genetically modified eukaryotic host cell, by virtue of introduction into a suitable eukaryotic host cell of a heterologous nucleic acid, e.g., an exogenous nucleic acid that is foreign to the eukaryotic host cell, or a recombinant nucleic acid that is not normally found in the eukaryotic host cell.

Before the present invention is described in greater detail, it is to be understood that this invention is not limited to particular embodiments described, which may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about," or "approximately." These terms "about," "approximate," or "approximately" are used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. Here again, it is understood that "about" a stated value includes a tenth of the unit above or below the stated value unless the context clearly dictates otherwise.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference in their entirety, as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the compositions and methods have been or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

DETAILED DESCRIPTION

The characteristic impairments (social and repetitive behaviors) of autism spectrum disorder (ASD) have major impact on quality of life, yet there are no approved medications that effectively treat these core features. Accumulating preclinical research suggests that arginine vasopressin (AVP), a neuropeptide involved in mammalian social functioning, may be a possible treatment for ASD. Using a double-blind, randomized, placebo-controlled, parallel design, the efficacy and tolerability of 4-week intranasal AVP treatment was tested in a sample of N=30 children with ASD aged 6-12 years. AVP compared to placebo treatment significantly enhanced social abilities in children with ASD as assessed by change from baseline in the trial's primary outcome measure, the Social Responsiveness Scale (a parent-report measure). AVP-related social improvements were likewise evident on clinician evaluated and child performance-based measures. When pre-treatment blood vasopressin levels were taken into consideration, AVP treatment was found to be more effective in autistic children having higher vasopressin levels; furthermore, in these children, AVP was also found to diminish not only anxiety symptoms but also some repetitive behaviors. Anxiety is a comorbid feature, but repetitive behaviors are a core diagnostic symptom of ASD. The majority of the symptoms and/or behaviors were more pronounced when pre-treatment bodily-fluid-based biological measures were accounted for (e.g., pre-treatment blood levels of vasopressin). AVP was well tolerated with minimal side-effects. No AVP-treated participant dropped out of the trial, and there were no differences in adverse event rates reported between the AVP and placebo treatment groups. Finally, no significant changes from baseline were observed in electrocardiogram, vital signs, height and weight, or clinical chemistry measurements after 4-week AVP treatment. These results suggest that intranasally administered AVP is a well-tolerated and promising medication for the treatment of ASD.

An accumulating body of research points to the vasopressin signaling pathway as a promising ASD target. It has been known for several decades that AVP plays a significant role in promoting mammalian social behavior (3) and that dysregulation of the AVP signaling pathway produces social deficits in rodents (4, 5). Researchers have begun to translate these preclinical findings to evaluate the effects of intranasal AVP administration on social and cognitive abilities in adult humans. These studies have shown that single-doses of intranasal AVP enhance a variety of social abilities including memory for emotional faces (6), identification of social words (7), and cooperative behavior (8) in healthy individuals. Single-doses of intranasal AVP have also been shown to enhance speech and word formation in patients with post-stroke aphasia (9) and to improve short and long-term memory in patients with central diabetes insipidus (10), suggesting cognitive enhancing properties of this drug. Although the precise mechanism by which AVP achieves these behavioral effects remains to be determined, intranasal AVP administration results in elevated cerebrospinal fluid (CSF) concentrations of measured AVP, suggesting that intranasally administered AVP achieves access to the central nervous system (11).

Because the pharmacological effects of AVP are especially evident in male animals (16, 20), and given ASD's male-biased prevalence (21), the AVP signaling pathway (any the possibility of sexual dimorphism in the prevalence and/or particular symptoms of ASD) are of interest toward understanding the risk for, and treatment of, ASD. However, before the present disclosure, the effects of intranasal AVP treatment in children with ASD had not been studied. Until the use of intranasally administered ASD in humans is performed and studied experimentally, the previous studies in adult humans and other animals (while useful), are not predictive, and the skilled artisan would have no reasonable expectation that the presently disclosed administration of intranasal vasopressin would be effective in treating ASD. As just one example supporting the unexpected nature of the results disclosed herein using AVP, experiments using intranasal administration of desmopressin were not found to effectively treat ASD in children.

Here, a double-blind, randomized, placebo-controlled, parallel design was used to test the efficacy and tolerability of 4-week intranasal AVP treatment in children with ASD aged 6-12 years. The central hypothesis was that AVP compared to placebo treatment would improve social abilities in children with ASD. The primary outcome measure was change from baseline in social ability as determined by parent ratings on the Social Responsiveness Scale, $2^{nd}$ Edition (SRS-2) Total Score, expressed as a gender-normed T-Score. Secondary outcome measures included change from baseline in social communication symptoms and social cognition abilities as assessed, respectively, by clinician evaluation and child performance on laboratory tasks. Also tested were (a) whether AVP treatment ameliorated other core or associated symptoms of ASD using parent rating scales, and (b) whether AVP is safe and well tolerated in individuals with ASD, since limited safety and tolerability data are available on its repeated intranasal administration in humans. Finally, tests were performed to assess whether pre-treatment measures of neuropeptide biology (e.g., pre-treatment blood AVP concentrations and blood neuropeptide receptor gene expression levels) predicted treatment response.

As disclosed in detail hereinbelow, a method of treating/ameliorating ASD in a subject diagnosed with ASD is described, the method comprising administering intranasal AVP, or an analog of vasopressin, to a subject having a high endogenous pre-treatment blood level of vasopressin (e.g., (a) greater than about 25% or more above the mean/normal pre-treatment vasopressin blood levels of a control subject or group of subjects (diagnosed or not diagnosed with ASD), and/or (b) ranging between 0.01 to 6.5 pg/mL endogenous pre-treatment vasopressin blood levels, whereby at least one measure of social impairment, anxiety, or repetitive behaviors is treated and/or ameliorated.

In some embodiments, no difference in pre-treatment blood AVP levels is observed between control and ASD subjects. It was unexpectedly observed that AVP treatment was more effective in subjects having high pre-treatment AVP levels (above the mean pre-treatment AVP blood level of a control group). In some embodiments, "high" levels, with respect to endogenous AVP, means that the pre-treatment levels of AVP in the blood (or other bodily fluid) are above the mean/average of the mean calculated from the range of pre-treatment endogenous levels.

In some embodiments, the endogenous pre-treatment blood vasopressin level in the subject is greater than ($\geq$) about 0.025 pg/mL, or $\geq$about 0.03 pg/mL, or $\geq$about 0.04 pg/mL, or $\geq$about 0.05 pg/mL, or $\geq$about 0.1 pg/mL, or $\geq$about 0.25 pg/mL, or $\geq$about 0.5 pg/mL, or $\geq$about 1.0 pg/mL, or $\geq$about 2.0 pg/mL, or $\geq$about 3.0 pg/mL, or $\geq$about 4.0 pg/mL. In some embodiments, the range of endogenous pre-treatment blood vasopressin levels in the subject is between about 0.025 pg/mL and about 6.0 pg/mL, and the mean pre-treatment endogenous blood vasopressin level of this range is approximately 3.01 pg/mL. In some embodiments, the range of endogenous pre-treatment blood vasopressin levels in the subject is or between about 0.1 and about 5 pg/mL, and the mean pre-treatment endogenous blood vasopressin level of this range is approximately 2.55 pg/mL. In some embodiments, the range of endogenous pre-treatment blood vasopressin levels is between about 0.05 and about 3.5 pg/mL, and the mean pre-treatment endogenous blood vasopressin level of this range is approximately 1.775 pg/mL. In some embodiments, the range of endogenous pre-treatment blood vasopressin levels in the subject is greater than about 0.04 pg/mL. and less than about 4.5 pg/mL, and the mean pre-treatment endogenous blood vasopressin level of this range is approximately 2.27 pg/mL. In some embodiments, the subject is a child under age 18, and the range of endogenous pre-treatment levels is between 0.045 and 4.028 pg/mL, and the mean pre-treatment endogenous blood vasopressin level of this range is approximately 2.037 pg/mL.

In some embodiments, the subject is a child between 6 and 12 years of age, and the range of endogenous pre-treatment levels is between 0.045 and 4.028 pg/mL, the mean pre-treatment endogenous blood vasopressin level is 1.324 pg/mL. In some embodiments, a "high pre-treatment blood level of vasopressin" is 10% above the mean. In some embodiments, a "high pre-treatment blood level of vasopressin" is 20% above the mean. In some embodiments, a "high pre-treatment blood level of vasopressin" is 25% above the mean. In some embodiments, a "high pre-treatment blood level of vasopressin" is 50% above the mean. In some embodiments, a "high pre-treatment blood level of vasopressin" in the subject is above 1.324 pg/mL. In some embodiments, a "high pre-treatment blood level of vasopressin" is 1.59 pg/mL. In some embodiments, a "high pre-treatment blood level of vasopressin" is 1.456 pg/mL. In some embodiments, a "high pre-treatment blood level of vasopressin" is 1.655 pg/mL. In some embodiments, a "high pre-treatment blood level of vasopressin" is 1.986 pg/mL. In some embodiments, a "high pre-treatment blood level of vasopressin" is 2.0 pg/mL.

In some embodiments, no difference in pre-treatment blood AVP levels is observed between control and ASD subjects, and thus, it was unexpected that AVP treatment was more effective in subjects having high pre-treatment AVP levels (above the mean pre-treatment AVP blood level of a control group). In some embodiments, the whole range of subjects responded to intranasal AVP treatment, and the surprising observation was that the response to the treatment was greater for those patients at the higher (above the mean) pre-treatment AVP levels.

In some embodiments, the vasopressin analog is lysine vasopressin.

In some embodiments, no difference in pre-treatment blood AVP levels is observed between control and ASD subjects.

In some embodiments, the range of endogenous pre-treatment blood vasopressin levels in the subject is greater than about 0.04 pg/mL and less than about 4.5 pg/mL. In some embodiments, the subject is a child under age 18, and the range of endogenous pre-treatment levels is between 0.045 and 4.028 pg/mL.

In some embodiments of the method, the measurement of social impairment, anxiety, and/or repetitive behaviors is determined based on a scale selected from the Social Responsiveness Scale (SRS), or one of its subscales, (e.g., the Social Communication and Interaction (SCI) subscale, and/or the restricted interests and repetitive behavior (RRB) subscale), the Clinical Global Impression-Improvement (CGI-I) scale, the Reading the Mind in the Eyes Test (RMET), the Facial Emotion Recognition Test (FERT), Spence Children's Anxiety Scale (SCAS), and the Repetitive Behaviors Scale-Revised (RBS-R). Anxiety is a comorbid feature of ASD, and repetitive behaviors are a core diagnostic symptom.

In some embodiments, the method treats social impairment and the social impairment is a simple social perceptual ability. In some embodiments, the method treats social impairment and the social impairment is a simple social perceptual ability. In some embodiments, the method treats social impairment and the social impairment is a complex social functioning ability. In some embodiments, the method treats anxiety associated with ASD. In some embodiments, the repetitive behavior manifests in the subject as a self-injurious behavior. In some embodiments, the method treats a restricted repetitive behavior.

In some embodiments of the method, the subject is 18 years of age or younger. In some embodiments, the subject is a child between 6 and 12 years of age.

In some embodiments of the method, the subject is administered intranasal AVP twice daily. In some embodiments, the subject is administered up to 16 IU AVP, between one and four times daily, (i.e., once, twice, thrice, or four times daily). In some embodiments, the subject is between 6 and 9.5 years of age and is administered intranasal AVP at a dose of about 12 IU twice daily. In some embodiments, the subject is between 9.6 and 13 years of age and is administered intranasal AVP at a dose of about 16 IU twice daily.

In some aspects, disclosed herein is a method of stratifying a population of pediatric subjects diagnosed with ASD into groups of subjects that are candidates for different effective dosage regimens, comprising measuring pre-treatment blood concentration of endogenous vasopressin in the population; and (i) assigning subjects having a pre-treatment endogenous vasopressin blood concentration of at least 0.045 pg/mL or more to a group to which a regimen of intranasally administered AVP begins at a lower effective dose and optionally increases to a higher dose; and/or (ii) assigning subjects having a pre-treatment endogenous vasopressin blood concentration of between about 0.04 pg/mL and about 2.5 pg/mL to a treatment group to which a regimen of intranasally administered AVP may be effective at a low dose, thereby stratifying the population of pediatric subjects having ASD into groups of subjects that are candidates for different effective dosage regimens.

In some embodiments the method of stratifying further comprises assigning genetically male subjects and genetically female subjects into separate subgroups.

In some aspects, disclosed herein is the use of a measure of the concentration of endogenous vasopressin in a bodily fluid selected from blood, serum, plasma, sputum, urine, and CSF, to determine an effective dose of intranasally administered AVP or an analog thereof. In some aspects, disclosed herein is the use of a measure of the concentration of endogenous vasopressin in a bodily fluid selected from blood, serum, plasma, sputum, urine, and CSF, to identify a subgroup within a pediatric population as treatable with low-dose intranasally administered AVP or an analog thereof, wherein the subgroup comprises individuals within the group having "high" levels of endogenous vasopressin as compared to subjects having "normal" or "low" concentrations.

Results

Participant Characteristics, Blinding Procedures. And Dosing Compliance

Figure 1:
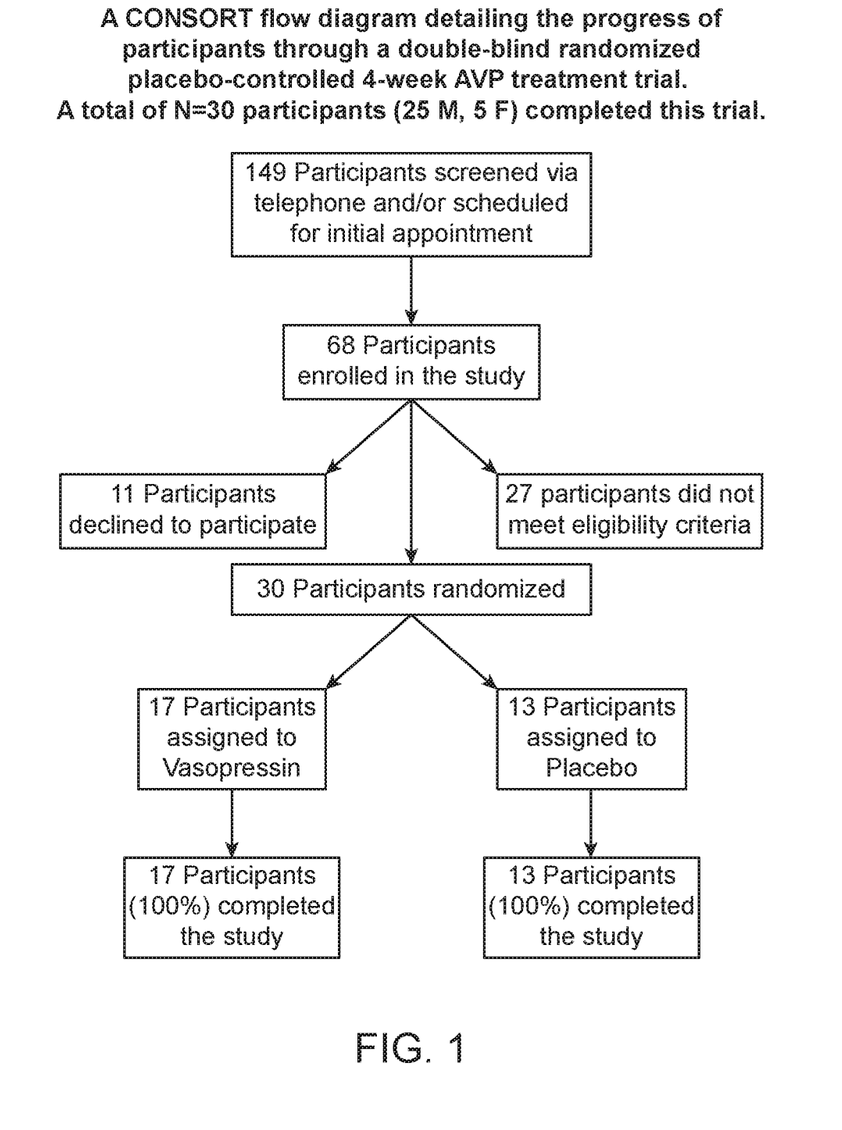
FIG. 1: illustrates a CONSORT flow diagram for the phase 2 clinical trial.

An a priori power analysis determined that N=30 participants were a sufficient sample for these analyses. A Consolidated Standards of Reporting Trials (CONSORT) flow diagram is shown in FIG. 1. The CONSORT flow diagram details participant progress, from screening to study completion, in double-blind randomized placebo-controlled testing of 4-week intranasal AVP treatment versus placebo in children with ASD. A total of 149 prospective participants were screened. Thirty-eight of the 68 individuals enrolled in the study were not randomized owing to either not meeting eligibility criteria or declining to participate. A total of N=30 participants (25 male, 5 female) were randomized to a treatment condition or placebo, and all 30 participants, independent of whether they were in the vasopressin or placebo group, completed the trial. Participant demographic and phenotypic characteristics are presented in Table 1.

TABLE 1

Participant Characteristics

| Treatment | N | Sex F | Sex M | Ethnicity Caucasian | Ethnicity Other | Age (yrs) | Full-Scale IQ Score | SRS-2 T-Score | CGI Severity Score | Blood AVP Level | Blood AVPR1A:OXTR |
|---|---|---|---|---|---|---|---|---|---|---|---|
| AVP | 17 | 3 | 14 | 8 | 9 | 9.14 ± 0.57 | 77.65 ± 5.03 | 70.29 ± 1.47 | 4.82 ± 0.15 | 1.32 ± 0.25 | 2.25 ± 0.31 |
| Placebo | 13 | 2 | 11 | 11 | 2 | 9.86 ± 0.65 | 91.85 ± 5.76 | 74.15 ± 1.68 | 4.77 ± 0.17 | 1.28 ± 0.29 | 2.21 ± 0.35 |

Abbreviations:
AVP, arginine vasopressin; F, female; M, male; IQ, intelligence quotient; SRS-2, Social Responsiveness Scale, $2^{nd}$ Edition; CGI, Clinical Global Impression; AVPR1A:OXTR, relative gene expression as the ΔΔCT of AVP 1A receptor and oxytocin receptor expression levels. Fisher's exact test was used to test whether the distribution of individuals randomized to the treatment conditions differed by sex and by ethnicity; no significant effects were found. For age, IQ, pre-treatment SRS-2 T-Score, pre-treatment CGI Severity Score, pre-treatment blood AVP level, and pre-treatment blood AVPR1A:OXTR expression, differences between treatment groups were tested with a simple one-way general linear model; no significant effects were discerned. The values are reported as mean ± standard error.

Participants' stable concomitant medications, which did not differ between treatment conditions, are presented in Table 2.

TABLE 2

Participants' stable concomitant psychotropic medications during the 4-week treatment trial.

| Medication | AVP (N = 17) | Placebo (N = 13) |
|---|---|---|
| SSRI | 1 (6%) | 2 (15%) |
| Other antidepressant | 0 (0%) | 1 (8%) |
| Antipsychotic | 0 (0%) | 1 (8%) |
| Benzodiazepine | 0 (0%) | 1 (8%) |
| Stimulant | 2 (12%) | 2 (15%) |
| Anti-epileptic | 0 (0%) | 1 (8%) |
| NMDAR antagonist | 1 (6%) | 0 (0%) |
| Guanfacine | 1 (6%) | 3 (23%) |
| Melatonin | 0 (0%) | 3 (23%) |
| Atomoxetine | 1 (6%) | 0 (0%) |

Abbreviations: arginine vasopressin (AVP); selective serotonin reuptake inhibitor (SSRI); N-methyl-D-aspartate receptor (NMDAR). Medication classes are reported as counts and percentages. Fisher's Exact Test was used to test for differences in concomitant medications between the AVP and placebo treatment groups, No significant differences were discerned.

Because the clinical trial's primary, and many of its secondary, outcome measures relied on parent report measures, multiple precautions were taken to keep the study blinded as described in Materials and Methods. Whether parents were able to ascertain the treatment condition to which their child had been randomized before breaking the study's blind was also empirically evaluated. Parents were not able to do so accurately (χ2 likelihood ratio, 0.002; P=0.9607), suggesting that parent ratings were not influenced by inadvertent knowledge of their child's treatment condition. Dosing compliance was also monitored in several ways as described in Materials and Methods. Compliance was also empirically evaluated by weighing participants' spray bottles after completion of the 4-week trial. Bottle weights did not differ between treatment conditions (AVP, 60.2±1.24 g versus placebo, 59.1±1.30 g; F1,21=0.3487; P=0.5611), suggesting that these results were not driven by treatment condition-related variations in dosing compliance.

Figure 2A:
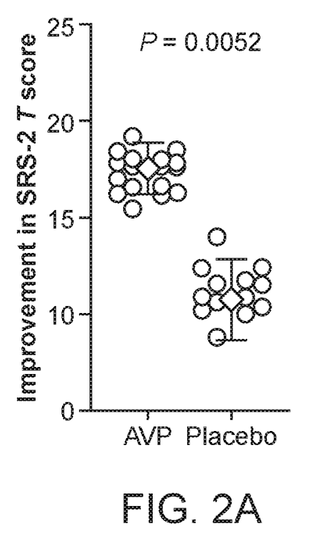
FIG. 2: shows the improvement scores for participants receiving 4-week intranasal arginine vasopressin (AVP) treatment versus placebo (shown at the mean blood vasopressin level).
Figure 2B:
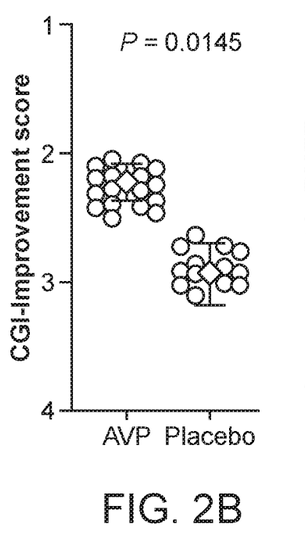
Figure 2C:
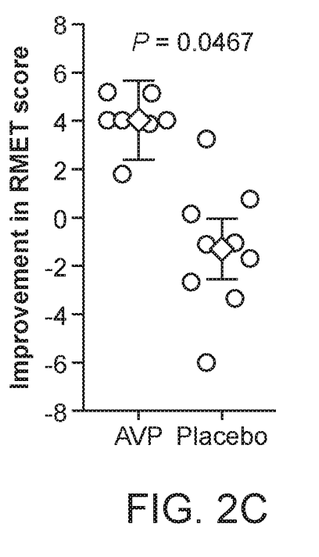
Figure 2D:
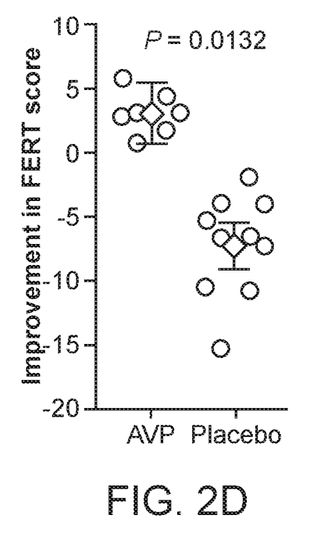
Figure 2E:
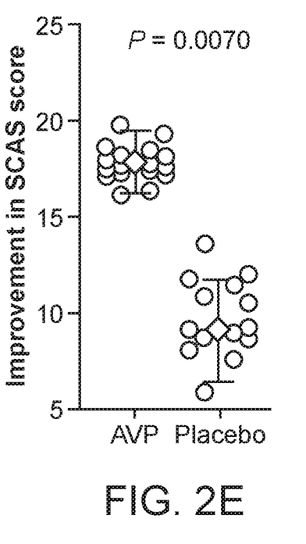
Figure 2F:
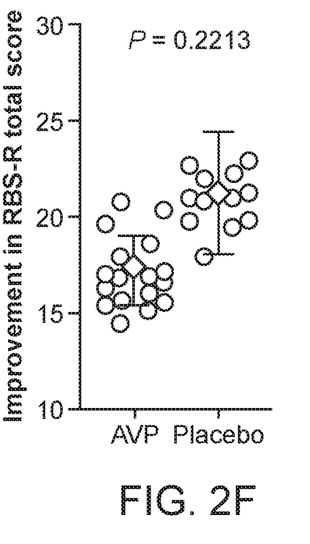

AVP Treatment Effects on Social Abilities: Primary and Secondary Outcome Measures Individuals with ASD treated with intranasal AVP for four weeks showed greater improvement in social abilities as assessed by the primary outcome measure, the SRS-2 T-Score, compared to those individuals receiving placebo ($F_{1,20}$=9.853; P=0.0052; $\eta_p^2$=33.0%; equivalent Cohen's d=1.40; FIG. 2, A; Table 3). This effect was also dependent on pre-treatment AVP concentrations in the blood ($F_{1,20}$=50.49; P<0.0001; $\eta_p^2$=71.6%; Table 3).

FIG. 2 shows improvement scores for participants receiving 4-week intranasal AVP treatment versus placebo. Participants' improvement scores for the clinical trial's key primary and secondary outcome measures are provided for each treatment condition. (FIG. 2 A) The primary outcome measure was the Social Responsiveness Scale, 2nd Edition (SRS-2) T score. (FIG. 2 B to F) The secondary outcome measures were the Clinical Global Impression (CGI)-Improvement score (B), Reading the Mind in the Eyes Test (RMET) score (C), Facial Emotion Recognition Test (FERT) score (D), Spence Children's Anxiety Scale (SCAS) score (E), and Repetitive Behaviors Scale-Revised (RBS-R) total score (F). General linear model F tests were used to evaluate whether participants treated with AVP (orange circles) versus placebo (blue circles) differed as a main effect of treatment (i.e., at the mean pre-treatment blood AVP concentration). Data are presented as least-squares means (LSM)±SEM, with individual data points plotted as residuals from their LSM adjacent to the respective error bar. Thus, all data are plotted corrected for other variables in the analysis. Data depicted in (A) and (C) to (F) are presented as absolute difference scores (between posttreatment and baseline pre-treatment) such that positive numbers on the y axis indicate improvement. Data depicted in (B) are presented as clinician improvement ratings where 1=very much improved since the initiation of treatment, 2=much improved, 3=minimally improved, and 4=no change since the initiation of treatment. AVP-treated participants differed significantly from placebo-treated participants in their improvement scores on nearly all measures except for the RBS-R, in which there was no overall group difference. n=30 for the SRS, CGI, and SCAS; n=29 for the RBS-R; n=17 for the FERT; and n=16 for the RMET.

TABLE 3

Change from baseline in the behavioral outcome measures for the 4-week treatment trial

| Measure | Treatment condition main effect | Improvement in score LSM +/- SE AVP | Improvement in score LSM +/- SE Placebo | Significant after correction? | Tx condition by pre-Tx blood AVP level | Significant after correction? | Is improvement in score greater or lesser with high pre-Tx blood AVP levels? AVP | Is improvement in score greater or lesser with high pre-Tx blood AVP levels? Placebo |
|---|---|---|---|---|---|---|---|---|
| Primary outcome measure | | | | | | | | |
| SRS-2 T-Score | $F_{1,20} = 11.60$; $P = 0.0028$ | 13.9 ± 1.12 | 7.83 ± 1.74 | * | $F_{1,20} = 56.26$; $P < 0.0001$ | * | Greater | Lesser |
| Social Awareness | $F_{1,20} = 3.714$; $P = 0.0683$ | 10.35 ± 1.29 | 5.78 ± 2.20 | ns | $F_{1,20} = 42.86$; $P < 0.0001$ | * | Greater | Lesser |
| Social Cognition | $F_{1,20} = 11.00$; $P = 0.0034$ | 19.33 ± 1.43 | 10.86 ± 2.39 | * | $F_{1,20} = 32.29$; $P < 0.0001$ | * | Greater | ns |
| Social Communication | $F_{1,20} = 5.658$; $P = 0.0275$ | 13.19 ± 1.90 | 7.20 ± 2.47 | ns | $F_{1,20} = 36.29$; $P < 0.0001$ | * | Greater | Lesser |
| Social Motivation | $F_{1,20} = 12.36$; $P = 0.0022$ | 19.19 ± 1.13 | 11.91 ± 1.95 | * | $F_{1,20} = 21.23$; $P = 0.0002$ | * | Greater | ns |
| Autistic Mannerisms | $F_{1,20} = 0.166$; $P = 0.6879$ | 16.51 ± 1.81 | 15.31 ± 2.77 | ns | $F_{1,20} = 3.719$; $P = 0.0681$ | ns | | |
| Secondary outcome measures (clinician rated) | | | | | | | | |
| CGI - Severity, Social & Communication | $F_{1,20} = 0.549$; $P = 0.4674$ | 0.873 ± 0.126 | 0.712 ± 0.202 | ns | $F_{1,20} = 1.519$; $P = 0.2320$ | ns | | |
| CGI - Improvement, Social & Communication | $F_{1,21} = 7.098$; $P = 0.0145$ | 2.23 ± 0.149 | 2.93 ± 0.244 | * | $F_{1,21} = 9.520$; $P = 0.0056$ | * | Greater | ns |
| Secondary outcome measures (parent rated) | | | | | | | | |
| Spence Children's Anxiety Scale | $F_{1,20} = 9.014$; $P = 0.0070$ | 17.9 ± 1.66 | 9.14 ± 2.68 | * | $F_{1,20} = 19.48$; $P = 0.0003$ | * | Greater | Lesser |
| RBS-R - Total | $F_{1,19} = 1.600$; $P = 0.2213$ | 17.2 ± 1.83 | 21.3 ± 3.18 | ns | $F_{1,19} = 18.57$; $P = 0.0004$ | * | Greater | ns |
| Stereotypy | $F_{1,19} = 0.001$; $P = 0.9783$ | 2.24 ± 0.313 | 2.23 ± 0.486 | ns | $F_{1,19} = 4.932$; $P = 0.0381$ | ns | | |
| Self-injurious behavior | $F_{1,19} = 0.552$; $P = 0.4666$ | 0.594 ± 0.467 | 1.18 ± 0.828 | ns | $F_{1,19} = 27.54$; $P < 0.0001$ | * | Greater | Lesser |
| Compulsive | $F_{1,19} = 2.028$; $P = 0.1707$ | 3.35 ± 0.511 | 4.59 ± 0.819 | ns | $F_{1,19} = 4.740$; $P = 0.0001$ | * | Greater | ns |
| Ritual | $F_{1,19} = 3.133$; $P = 0.0920$ | 3.08 ± 0.504 | 4.63 ± 0.818 | ns | $F_{1,19} = 3.643$; $P = 0.0708$ | ns | | |
| Sameness | $F_{1,19} = 0.043$; $P = 0.8375$ | 5.61 ± 0.66 | 5.85 ± 1.03 | ns | $F_{1,19} = 3.071$; $P = 0.0950$ | ns | | |
| Restricted | $F_{1,19} = 0.623$; $P = 0.4392$ | 2.58 ± 0.54 | 3.4 ± 1.01 | ns | $F_{1,19} = 4.261$; $P = 0.0522$ | ns | | |
| Secondary outcome measures (child performance) | | | | | | | | |
| Facial Emotion Recognition Test | $F_{1,7} = 10.85$; $P = 0.0132$ | 3.10 ± 2.42 | −7.19 ± 1.81 | * | $F_{1,7} = 0.971$; $P = 0.3573$ | ns | | |
| Reading the Mind in the Eyes Test | $F_{1,6} = 6.2341$; $P = 0.0467$ | 4.04 ± 1.63 | −1.28 ± 1.24 | * | $F_{1,6} = 0.068$; $P = 0.8031$ | ns | | |
| NEPSY - Theory of Mind | $F_{1,12} = 0.647$; $P = 0.4367$ | 2.1 ± 1.41 | 0.677 ± 1.20 | ns | $F_{1,12} = 1.162$; $P = 0.3022$ | ns | | |
| NEPSY - Affect Recognition | $F_{1,12} = 0.946$; $P = 0.3500$ | 0.094 ± 2.20 | −2.58 ± 1.90 | ns | $F_{1,12} = 0.251$; $P = 0.6254$ | ns | | |

Abbreviations used in Table 3 are:
Least Squares Mean (LSM); arginine vasopressin (AVP); Social Responsiveness Scale (SRS); Clinical Global Impressions Scale (CGI); the Repetitive Behaviors Scale-Revised (RBS-R); A Developmental NEuroPSYchological Assessment (NEPSY). Data were analyzed using the same model throughout [controlling for ethnicity, IQ, pre-treatment blood differential receptor gene expression, and baseline behavioral severity (for each measure)]. Analyses tested for a main effect of treatment condition at the mean pre-treatment ("pre-Tx") blood AVP concentration, given any selective effect of pre-treatment blood AVP concentration on treatment response (tested by the treatment condition by pre-treatment blood AVP concentration interaction). "CGI-Improvement" is a single score taken after 4-week treatment. Other scores are given as a change from baseline, normalized for the direction of the scale, so that improvement of symptoms could be reported as a positive change. For all measures, significant overall effects of treatment condition are in the predicted direction (i.e., AVP-treated participants improved more than placebo-treated participants). When a treatment condition-by-pretreatment blood AVP concentration interaction was significant, post-hoc tests were reported for AVP- and placebo-treated subjects: "greater" indicates that symptom improvement increased with higher pre-treatment blood AVP concentrations; "lesser" indicates that less improvement was observed at higher pre-treatment blood AVP concentrations; and "ns" indicates that the scale was not significantly affected by pre-treatment blood AVP concentration. "*" indicates statistical significance. Subscales of an instrument were only tested if the overall score was significant (P < 0.05) and were tested at appropriate Bonferroni corrected critical alphas to minimize the risk of false discovery (SRS critical alpha <0.01; RBS-R, critical alpha <0.0083). Any post-hoc tests of treatment group-by-pretreatment blood AVP concentration interactions are further Bonferroni corrected to a critical alpha half that of the original critical alpha for the interaction.

Higher pre-treatment blood AVP concentrations predicted a greater treatment response in AVP-treated participants ($F_{1,20}=60.13$; $P<0.0001$; Table 3), and lesser treatment response in placebo-treated participants ($F_{1,20}=22.49$; $P<0.0001$). The same pattern of results was observed if all study blocking factors were excluded, confirming the robustness of the model. Additionally, the core result of the treatment condition-by-AVP concentration interaction held if the model was not weighted by the reliability of pre-treatment parent-reported SRS T-Scores ($F_{1,20}=7.235$; $P=0.0141$). Finally, a similar pattern of results was observed in the SRS, as well as the SCI and RRB subscales, with AVP's treatment effects being most pronounced in the social motivation and social cognition domains (Table 3).

Parent ratings of AVP treatment-related improvement in social functioning were corroborated by blinded clinician evaluation and child performance on laboratory tasks (Table 3). Specifically, AVP-treated individuals showed greater clinician evaluated improvement in social communication abilities [as assessed by the Clinical Global Impression-Improvement (CGI-I) Scale] compared to placebo-treated individuals following 4-week AVP administration ($F_{1,21}=7.098$; P=0.0145). As with the SRS, this result was more pronounced in AVP-treated participants with higher pre-treatment blood AVP concentrations ($F_{1,21}=9.52$; P=0.0056).

Similarly, child participants treated with AVP vs. placebo showed enhanced theory of mind abilities (i.e., the ability to interpret others' mental/emotional states) as assessed by the Reading the Mind in the Eyes Test (RMET) ($F_{1,6}=6.2341$; P=0.047), as well as increased facial emotion recognition abilities as assessed by the Facial Emotion Recognition Test (FERT) ($F_{1,7}=10.85$; P=0.0132). The effects of AVP treatment on children's performance-related assessments were independent of pre-treatment blood AVP concentrations.

AVP Treatment Effects on Other Core and Associated Symptom Measures

AVP treatment reduced anxiety symptoms compared to placebo treatment as assessed by the Spence Children's Anxiety Scale ($F_{1,20}=9.014$; P=0.0070). As observed for social abilities, this effect, too, was magnified in AVP-treated participants with the highest pre-treatment AVP concentrations ($F_{1,20}=19.48$; P=0.0003). Although AVP compared to placebo as a main effect of treatment did not significantly reduce repetitive behaviors as assessed by the Repetitive Behaviors Scale-Revised (RBS-R), it did diminish repetitive behaviors overall (particularly self-injurious and compulsive behaviors), in AVP-treated participants with the highest pre-treatment blood AVP concentrations (See Table 3).

AVP Treatment Effects on Safety and Tolerability Measures

AVP was overall well tolerated with minimal adverse effects. No participants dropped out during this study. There were no significant differences in adverse event rates reported in the AVP-treated compared to placebo-treated groups as assessed by parent ratings on the Dosage Record and Treatment Emergent Symptom Scale (DOTES) and Overt Aggression Scale (OAS) No significant changes from baseline in vital signs, 12-lead electrocardiogram, clinical chemistry, or physiological measures were discerned after 4-week treatment (Table 4).

Discussion

Using a double-blind, randomized, placebo-controlled, parallel design, it was observed that 4-week AVP vs. placebo treatment significantly enhanced social abilities in children with ASD as assessed by the trial's primary outcome measure, the SRS-2 T-Score. The robustness of this parent-reported social improvement was corroborated by convergent evidence from clinician evaluation of participant social communication abilities and by child performance on laboratory tests of social cognition. These results suggest that intranasally administered AVP may be a promising medication for treatment of core social impairments in children with ASD.

Whether pre-treatment neuropeptide biology could predict AVP treatment response was also investigated. Participants with the highest pre-treatment blood AVP concentrations were found to benefit the most from AVP (but not placebo) treatment. At first blush, these results may seem counterintuitive, particularly in light of recent studies showing that low CSF AVP concentration differentiates ASD cases from controls (13, 22). One might therefore expect it would be those children with the lowest endogenous AVP concentrations that stood to benefit the most from AVP "replacement". However, being mindful of safety in this pediatric population, these studies used a conservative dose escalation regimen in which children were treated with low-dose AVP (as compared to AVP administered for other medical conditions). Assuming that blood AVP concentrations are related in some manner to brain AVP activity [a notion about which there is debate (22-26)], it is possible that participants with lower endogenous AVP concentrations at the trial's outset were "under-dosed" (in terms of drug amount and/or duration of treatment) and could not benefit as fully from AVP administration as those with higher endogenous AVP concentrations. This interpretation is consistent with the results presented herein demonstrating that AVP treatment enhanced simple social perceptual abilities independent of pre-treatment blood AVP concentration, whereas it was only those AVP-treated individuals with higher pre-treatment blood AVP concentrations that showed gains in complex social functioning, as well as a reduction in repetitive behaviors. These results point to the need for larger clinical trials to evaluate endogenous pre-treatment AVP concentration in relation to maximum tolerated AVP dose and outcome measures more directly related to brain function (e.g., electroencephalography) to determine whether pre-treatment blood AVP concentration may be a useful complementary diagnostic by which to establish AVP dosing guidelines.

AVP's actions are mediated by four G protein-coupled receptors [(i.e., AVPR1A, AVPR2, AVPR3 (also known as AVPR1B), and OXTR], which are distributed in a tissue-specific manner throughout the brain and body (27). In the brain, in addition to prosocial functioning, AVPRs and OXTR have been implicated in regulating stereotyped behaviors, anxiogenesis/anxiolysis, and territorial/parental aggression and mate-guarding [although their roles in these phenomena are complex and vary markedly by species, context, brain region, and receptor type (28, 29)]. AVPRs are also known for their peripheral roles in vasoconstriction, thrombosis, plasma volume and osmolality control, and anterior pituitary hormone release (27).

In fact, small molecule AVPR1A antagonists are currently being developed and tested by Hoffmann-La Roche to treat ASD. The rationale for treating ASD patients with an AVPR1A antagonist is based, at least in part, on studies showing that AVP administration increases aggression in male rodents (39, 40) and enhances threat perception in healthy adult male volunteers (41). However, these prior studies were conducted using "neurotypical" animal and human subjects, with presumably intact AVP neural circuitry. The AVP receptor antagonist molecules were identified through high throughput screening (37); one published study to date has reported on the effects of single dose intravenous administration of RG7713 in a small sample of high-functioning adults with ASD (38). This study reported non-significant AVP receptor antagonist-related improvements on overall composite tests, with a few post hoc sub-test findings (not corrected for multiple comparisons) showing that RG7713 increased biological motion orienting preference and reduced the ability to detect lust on an affective speech recognition task.

Children with ASD were found to have significantly lower CSF AVP concentrations compared to control children without ASD, and ASD patients with the lowest CSF AVP concentrations had the greatest symptom severity (12, 13). Animal models demonstrate that AVP's prosocial effects are largely mediated via AVP 1A receptors (AVPR1A) (14-18). AVP concentrations increase in both CSF and blood following intranasal administration of AVP (11), suggesting that a variety of neuropeptide receptor-mediated behavioral and physiologic processes might be affected—in both desirable and undesirable ways—by intranasal AVP treatment. Thus, historically, the belief has been that administration of AVP might lead to unwanted behavior such as aggression. In light of the aforementioned, the skilled artisan would not have expected that intranasal administration of AVP would be effective to treat social deficits in ASD.

However, in the studies described herein, the rationale for treating ASD patients with AVP began with some evidence of increased AVP release during social bond formation in rodents (16, 17, 20), as well as the observation that naturally low-social male rhesus monkeys and children display symptoms of ASD (12, 13, 42), and low CSF AVP concentration might be a marker of impaired social functioning in both species. Because ASD is clinically heterogenous, each AVP-related treatment and/or dosing strategy may ultimately depend on stratification of biologically well-characterized ASD subgroups having distinct symptoms.

In the present study, intranasal AVP treatment was found to reduce repetitive behaviors (particularly self-injurious and compulsive ones) as well as anxiety symptoms in children with ASD. Intranasal AVP treatment was determined to be safe, well tolerated, and had minimal side effects in the study population. It is worth noting, however, that participants in the study were required to have normal cardiac function, vital signs, and clinical chemistry values and be free of seizure disorders as well as serious liver, renal, and cardiac illnesses. Participants were also excluded if they habitually consumed high fluid volumes. The selected age range of treated participants (the majority of whom were male) was also overwhelmingly prepubertal (i.e., 6-12 years of age), out of consideration that testosterone can enhance AVP's aggression promoting effects, at least in male rodents (30). As AVP treatment trials expand to include higher dosing regimens and post-pubertal individuals, "off-target" AVP effects will continue to require careful monitoring.

A synthetic analogue of AVP, desmopressin (DDAVP), has been widely used for over 40 years to treat nocturnal enuresis (33). Nocturnal enuresis is common in individuals with ASD (34), but there are no reports that DDAVP enhances social functioning in ASD (or in any other clinical population). This may be because DDAVP is typically administered orally at bedtime; oral DDAVP does not cross the blood brain barrier (35). It is worth noting that DDAVP acts selectively at AVPR2, rather than AVPR1A (36).

The study participants were not medication free, but their concomitant medications were stable during the intervention. These medications were not known to interact with intranasal AVP and did not differ by treatment condition. It is therefore unlikely that the observed social improvements in AVP-treated individuals were driven by other medications. The primary outcome measure (and many of the secondary outcome measures) relied on parent reporting to ascertain AVP treatment-related changes. Although gold-standard reporting instruments were used, these measures were nevertheless subjective in nature. This subjectivity was mitigated, at least for the primary outcome measure, by accounting for measurable influences in parent SRS-2 score reporting reliability, and by determining that blinded clinician assessment and child performance on laboratory tests corroborated parent ratings. A measure of treatment-related change in clinical significance can be assessed, such as the brief observation of social communication change (44), a sensitive test designed specifically to assess changes in core ASD symptoms, particularly in the context of treatment trials.

In conclusion, the present study determined that 4-week intranasal AVP compared to placebo treatment significantly enhanced social abilities, diminished anxiety symptoms, and reduced repetitive behaviors in children with ASD. On nearly all behavioral measures, participants with the highest pre-treatment blood AVP concentrations benefitted the most from AVP (but not placebo) treatment, suggesting that pre-treatment blood AVP concentration may be useful as a complementary diagnostic for this medication. Finally, intranasal AVP treatment was well tolerated with minimal side effects in this pediatric study population. These results suggest that intranasal AVP treatment has potential to enhance social abilities in a patient population characterized by currently intractable social impairments.

Materials and Methods

Study Design and Regulatory Approval

This phase 2 clinical trial was conducted in the Autism and Developmental Disorders Clinic (ADDC) in the Division of Child and Adolescent Psychiatry at Stanford University. Recruitment began in December 2013 and ended in May 2017. Prior to initiating this trial, an Investigational New Drug application (#118327) was filed with the Federal Drug Administration and this study was approved by the Institutional Review Board of Stanford University. This trial was also registered on ClinicalTrials.gov (NCT01962870). Parents and/or legal guardians of the study's participants provided written consent prior to initiation of experimental procedures. If the child was deemed intellectually capable of understanding the study, written assent was also obtained. Finally, this study was overseen by an independent Data Safety Monitoring Board comprised of clinicians with expertise in clinical trials, ASD, or pediatric medical care.

Participant Recruitment and Eligibility Criteria

Children with a history of an ASD diagnosis were recruited to participate in this study. Participants were recruited through: 1) the Autism and Developmental Disorders Research Registry at Stanford University, 2) flyers posted in the ADDC or in the surrounding community (e.g., pediatrician offices), 3) advertisements posted online (e.g., Interactive Autism Network), or 4) special events (e.g., Autism Speaks Walk). Participants were phone screened for initial study eligibility, and then underwent a medical assessment as well as a comprehensive psychiatric evaluation. The psychiatric evaluation included a clinical interview to confirm the child's previous ASD diagnosis based on Diagnostic and Statistical Manual of Mental Disorders, Fourth Edition, Text Revision (DSM-IV-TR) (43), which was further ascertained by the Autism Diagnostic Instrument-Revised (44) and the Autism Diagnostic Observation Schedule, $2^{nd}$ Edition (45).

In addition to meeting diagnostic criteria for ASD, other study inclusion criteria included: 1) medically healthy outpatients between 6 and 12.92 years of age; 2) IQ>50 (as determined by the Stanford Binet $5^{th}$ Edition (46); 3) Clinical Global Impression Severity (CGI-S) Scale rating of ≥4 (47); 4) care provider who can reliably bring participant to clinic visits, provides trustworthy ratings, and interacts with the participant on a regular basis; 5) stable medications for at least 4 weeks; 6) no planned changes in psychosocial interventions during the trial; and 7) willingness and ability to provide blood samples and undergo electrocardiogram.

Study exclusion criteria included: 1) Prior or current use of AVP; 2) abnormal chemistry result; 3) electrocardiogram abnormality; 4) DSM-IV-TR diagnosis of schizophrenia, schizoaffective disorder, or psychotic disorder; 5) regular nasal obstruction or nosebleeds; 6) active medical problems: unstable seizures, significant physical illness (e.g., serious liver, renal, or cardiac pathology); 7) sensitivity to preservatives (e.g., chlorobutanol); 8) evidence of a genetic mutation known to cause ASD (e.g., Fragile X Syndrome); 9) significant hearing or vision impairments; 10) habitually drinks large volumes of water; 11) pregnancy, breastfeeding, or child birth within the last 6 months; or 12) sexually active females not using a reliable method of contraception. Additionally, any female aged 11 years or older, or who had started menstruating, was required to have a (negative) urine pregnancy test.

Pharmacological Intervention

Commercially available injectable sterile AVP was used in this study. It was initially purchased from JHP Pharmaceuticals (Rochester, MI), which was subsequently acquired by Par Sterile Products (Chestnut Ridge, NY) in 2014. The placebo solution was prepared by Koshland Pharm (San Francisco, CA) and consisted of ingredients used in the active solution except the AVP compound. A pharmacist transferred 25 mL of AVP (20 International Units (IU)/mL) or placebo solutions into sterile amber glass bottles with metered (0.1 mL/per puff) nasal spray applicators to ensure that the AVP and placebo applicators were visually indistinguishable to the research team. These applicators were coded and given to the Stanford Health Care's Investigational Drug Service (IDS) for refrigerated storage (2-8° C.) and subsequent dispensing. Following the first AVP dose (see below), the dose escalation regimen for all participants involved administration of 4 IU twice daily (or BID) of AVP during week 1 and 8 IU BID of AVP during week 2. Participants aged 6 to 9.5 years then received 12 IU BID of AVP during weeks 3 and 4, while participants aged 9.6 to 12.92 years received 16 IU BID of AVP during weeks 3 and 4.

Overview of Study Visits and Procedures

After the screening phase, baseline (pre-treatment) measures were obtained from participants continuing to meet inclusion and exclusion criteria. These measures included: assessments of participants' behavioral symptoms and abilities, safety/tolerability monitoring, and blood sample collection for later neuropeptide quantification. One to four weeks later, participants were randomly assigned to a treatment condition (i.e., AVP or placebo), stratified by age (6 to 9.5 vs. 9.6 to 12.92 years) and sex (M vs. F). Randomization was performed by an unblinded investigator using a machine-generated treatment schedule, which allocated each participant to an intervention by using the method of randomly permuted blocks of 2 or 4 (which were then concatenated together to form the schedule). This practice allowed the clinical research team to remain blinded throughout the trial's duration.

Parents were trained in the clinic by research staff to administer the nasal spray to their child. The first dose was administered in the ADDC under the direct supervision of the research team (with the first dose being 12 IU for participants aged 6 to 9.5 years and 16 IU for participants aged 9.6 to 12.92 years). Vital signs were monitored before, and 20 minutes after, initial single-dose nasal spray administration to monitor for acute, unanticipated reactions to AVP. Participants' parents then received two 25 mL nasal spray bottles containing either AVP or placebo for 4 weeks of at-home dispensing (as described above), for which they were responsible for their child's continued twice daily dosing. Parents were instructed to keep the bottles refrigerated with only brief room temperature excursions (i.e., for dosing). Participants underwent weekly safety/tolerability assessments in the clinic to monitor for adverse events. On completion of the 4-week treatment period, behavioral data, safety/tolerability data, and blood samples were again collected. After completion of the trial, participants randomized to the placebo group were invited to participate in an optional open-label 4-week AVP treatment phase to ensure that all children had the opportunity to receive AVP treatment.

Laboratory Social Cognition Tests

In addition to parent-rated questionnaires and clinical evaluation of behavioral symptoms (detailed below), children were assessed at baseline and following 4-week treatment on laboratory tests of social functioning designed to assess the ability to perceive others' intentions or emotions. These tests included: the 28-item child RMET, which consists of images of eyes depicting emotional states and from which the participant makes a forced choice from four mental state terms per image (48), the Developmental NEuroPSYchological Assessment, $2^{nd}$ Edition, Social Perception Domain subtests of Affect Recognition (which assesses the ability to recognize affect from photographs of children's faces) and Theory of Mind (which assesses the ability to understand complex mental functions through a series of visual and verbally presented stories and questions (49), and the FERT, which was derived from the NimStim Set of Facial Expressions (50). Here the FERT required participants to identify the correct facial emotion displayed by each face stimulus. In the FERT, participants were required to select an emotion from a list of 7 possible emotions (angry, calm, disgusted, happy, sad, scared, surprised) and were administered a total of 42 face stimuli per test session.

Safety and Tolerability Monitoring

Throughout the trial, safety and tolerability were assessed weekly using the following measurements: vital signs, 12-lead electrocardiogram, clinical chemistry labs, and height and weight. Side effects were evaluated with the DOTES (51), and modified to assess potential side effects that might be related to AVP such as hyponatremia/water intoxication. Finally, based on animal studies showing that AVP can induce aggressive behavior under some circumstances (39, 40), the OAS was used to monitor for observable aggressive or violent behavior in this trial (52).

Blood Sample Collection and Processing Procedures

Whole blood was drawn from the child's antecubital region by a pediatric phlebotomist using standard protocols at Lucile Packard Children's Hospital outpatient laboratory. A portion of the sample was collected per standard laboratory protocols and sent for clinical chemistry analysis. To evaluate AVP concentrations, whole blood was also collected into chilled EDTA-treated vacutainer tubes and immediately placed on wet ice. Samples were promptly centrifuged (1600×g at 4° C. for 15 min), the plasma fraction aliquoted into polypropylene tubes, and flash-frozen on dry ice. Whole blood was also collected into PAXgene RNA tubes (Qiagen, CA) and processed per manufacturer instruction to evaluate neuropeptide receptor gene expression [i.e., oxytocin receptor (OXTR) and AVPR1A]. All samples were stored at −80° C. until quantification.

Quantification of Blood AVP Concentrations

AVP concentrations were quantified using a commercially available enzyme immunoassay kit (Enzo Life Sciences, Inc., Farmingdale, NY). This kit is highly specific and selectively recognizes AVP and not related peptides (i.e., cross-reactivity with OXT is <0.001%). A research team member blinded to treatment condition performed sample preparation and AVP quantification following established procedures (12, 22). Briefly, blood samples (1000 μL/participant) were extracted per manufacturer's instructions and evaporated using compressed nitrogen. Each evaporated sample was reconstituted in 250 μL of assay buffer prior to AVP quantification to provide sufficient sample volume to run each participant's sample in duplicate wells (100 μL/well). This practice ensured that the plated samples contained high enough AVP quantities to be read above the limit of detection (2.84 pg/mL). Samples were assayed with a tuneable microplate reader (Molecular Devices, CA) for 96-well format per manufacturer's instructions. Intra- and inter-assay coefficients of variation were below 10%.

Quantification of Blood OXTR and AVPR1A Gene Expression Levels

Total RNA was isolated and purified using a PAXgene blood RNA kit from blood stabilized in PAXgene RNA tubes (Qiagen, CA). RNA integrity was assessed with the Agilent 2100 Bioanalyzer (Agilent Technologies, CA), and consistently found to have RIN values (RNA integrity numbers) greater than 9.5. The first strand cDNA synthesis reaction was carried out with QuantiTect reverse transcription kit (Qiagen, CA), with a starting RNA quantity of 1 μg in a 20 μl final volume. The primer sequence information for OXTR and AVPR1A genes was obtained from published studies and was designed as follows: OXTR forward 5'-CTGAA-CATCCCGAGGAACTG-3' (identified herein as SEQ ID NO: 1) and reverse 5'-CTCTGAGCCACTGCAAATGA-3' (identified herein as SEQ ID NO: 2) (53); AVPR1A forward 5'-CTTTTGTGATCGTGACGGCTTA-3' (identified herein as SEQ ID NO: 3) and reverse 5'-TGATGGTAGGGTTTTCCGATTC-3' (identified herein as SEQ ID NO: 4) (54). Two housekeeping genes, hypoxanthine phosphoribosyltransferase 1 [HPRT1; forward 5'-GGACAGGACTGAACGTCTTGC-3' (identified herein as SEQ ID NO: 5) and reverse 5'-ATAGCCCCCCTT-GAGCACAC-3' (identified herein as SEQ ID NO: 6) (54)] and ubiquitin C [UBC; forward 5'-GCTGCTCATAA-GACTCGGCC-3' (identified herein as SEQ ID NO: 7) and reverse 5'-GTCACCCAAGTCCCGTCCTA-3' (identified herein as SEQ ID NO: 8) (54)] were selected for normalization using geNorm. qPCR was performed on the StepOnePlus Real-Time PCR System (Life Technologies, CA) with SYBR Green (Thermo Fisher Scientific, MA). cDNA was PCR amplified in triplicate and Ct values from each sample were obtained using StepOnePlus software. The relative expression of each gene was calculated based on the $\Delta\Delta$Ct value, where the results were normalized to the average Ct value of HPRT1 and UBC (55).

Trial Outcome Measures

The trial's primary outcome measure was change from baseline in social ability as assessed by parent ratings on the SRS-2 T-Score. The SRS measures the severity of social communication deficits as they occur in natural environments. The SRS is a sensitive measure (i.e., it strongly correlates with DSM criterion scores) (56), and has been used as a primary measure of response to intervention in prior clinical trials (57-60).

The trial's secondary behavioral outcome measures included social improvement assessed by child performance on laboratory tests (as detailed above), and symptom improvement in other core or associated non-social symptom domains. CGI-S and CGI-I Scales were also obtained and were completed by a clinician with extensive experience in the assessment and treatment of children with developmental disabilities (47). The CGI-S uses a 7-point scale ranging from not at all ill (1) to extremely ill (7). The CGI-I uses a 7-point scale ranging from marked improvement (1) to no change (4) to very much worse (7). In this study, the ratings were specifically focused on social communication skills.

Treatment effect generalizability was evaluated using: 1) the RBS-R which measures a comprehensive list of repetitive and stereotyped behaviors (61); and 2) The Spence Children's Anxiety Scale which assesses the severity of trait anxiety symptoms broadly in line with DSM dimensions of anxiety disorder (62). Anxiety was selected as an outcome measure due to its significant comorbidity with ASD (63). Finally, safety and tolerability were evaluated using: 1) the DOTES (51); and 2) change from baseline in electrocardiogram, clinical chemistry labs, vital signs (i.e., blood pressure, heart rate, temperature), as well as height and weight.

Statistical Analyses

Data were managed using REDCap (64) and analyzed using Least-Squares General Linear Models (LS-GLMs) in JMP Pro 13 and SAS 9.4 for Windows (SAS Institute Inc., Cary, NC). Efficacy analyses were guided by the pre-study aims which included: 1) testing for treatment main effects on the primary and secondary outcome measures; and 2) determining whether pre-treatment blood-based biological measures predicted who benefited from treatment. To minimize the risk of false discovery, a robust model using the primary outcome measure (i.e., change in the SRS-2 T-Score) was first developed.

The initial model included gender, ethnicity, weight, IQ, and blood collection time as blocking (control) factors. Pre-treatment SRS-2 T-Score was included as a blocking factor to account for the range of possible improvement, and thus reduce possible floor or ceiling effects. Finally, to test the main hypothesis, treatment condition (i.e., AVP or placebo) was included and pre-treatment blood AVP concentration and pre-treatment blood neuropeptide receptor gene expression level (expressed as an AVPR1A-to-OXTR ratio to account for within-individual differences in expression) were used as measures of endogenous AVP function that might predict treatment efficacy. As two different AVP doses were administered according to age, dose was nested within treatment condition to explicitly test for an overall effect of AVP treatment, and secondarily to control for any dose-related effects. Also tested were treatment condition×biological measure and dose×biological measure interactions, as pre-treatment biological measures should generally only predict treatment outcome in the drug-treated individuals. Finally, because the SRS is a parent-reported measure, SRS scores were collected at two pre-treatment time points to identify the reliability of an individual participant's scores. This enabled us to use Weighted Least-Squares General Linear Model (WLS-GLM) analyses whenever parent-reported measures were assessed. WLS ideally uses the inverse of the variance of a mean estimate as the weight, which could be obtained directly from the two pre-treatment SRS scores.

Initial analyses showed that gender, blood collection time, and weight introduced collinearities, were non-significant, and did not improve the $R^2$ of the model, and so were removed following best practice for linear models (model simplification is important to avoid over-specification, and the associated risk for false discovery, especially in small sample sizes) (65). In particular, gender was collinear with IQ, and so could be safely removed from the model while still being controlled for in the analysis. Similarly, non-significant interactions were removed in order to avoid confounds of marginality for the main effects, and to distinguish blocking factors. The final model contained ethnicity, IQ, pre-treatment SRS-2 T-Score, and AVPR1A-to- OXTR gene expression ratio as blocking (control) variables. Dose nested within treatment condition and pre-treatment blood AVP concentration were tested as main effects, as well as the interaction of pre-treatment blood AVP concentration with dose-nested-within-treatment condition. Thus, the model contained the biologically and experimentally essential variables, regardless of significance. An effect size for the primary outcome measure was calculated as $\eta_p^2$ (partial eta-squared). The robustness of this model was tested by confirming key results held for this model if all blocking factors were included and if WLS-GLM was not employed.

Once this model was confirmed for the primary outcome measure, the same model was applied to all secondary outcome measures with the exception that the baseline, pre-treatment behavioral measure was replaced to match the outcome variable. For child performance measures, LS-GLM, not WLS-GLM, was used (and WLS-GLM did not improve these models confirming that the WLS-GLM approach was specific to parent-rated measures by capturing variance in parent ratings). For CGI-Improvement, in which there is no baseline pre-treatment measure, the model did not include a baseline control.

To minimize the risk of false discovery from multiplicity (65), the total score for each instrument was first tested, and then subscales were only tested if the total score was significant. Subscales were Bonferroni-corrected for multiple comparisons. The assumptions of WLS-GLM (linearity, homogeneity of variance, and normality of error) were confirmed post-hoc and suitable transformations applied as needed (65). Post-hoc tests were performed as planned contrasts and further Bonferroni-corrected for multiple comparisons. As these models consistently showed an interaction between treatment condition and pre-treatment blood AVP concentration (i.e., pre-treatment blood AVP concentration predicted the magnitude of the behavioral response to drug), the first aim was to test for an overall effect of treatment condition at the mean pre-treatment blood AVP concentration.

One-way LS-GLMs were used to test the change from baseline between the AVP and placebo treatment groups following 4-week treatment for adverse events and safety measures. Fisher's exact Test was used to test for differences between treatment conditions for participant characteristics and concomitant medications. Suitable transformations were applied as needed.

TABLE 4

Reported adverse events during the 4-week treatment trial assessed by the DOTES and OAS

| Adverse Event | AVP (N = 17) | Placebo (N = 13) |
|---|---|---|
| General | | |
| Fever | 2 (12%) | 1 (8%) |
| Cough | 1 (6%) | 0 (0%) |
| Body ache | 1 (6%) | 0 (0%) |
| Neurological/Psychiatric | | |
| Excitement/agitation | 4 (24%) | 1 (8%) |
| Insomnia | 4 (24%) | 1 (8%) |
| Increased motor activity | 4 (24%) | 0 (0%) |
| Depressive affect | 2 (12%) | 1 (8%) |
| Headache | 2 (12%) | 0 (0%) |
| Drowsiness | 1 (6%) | 3 (23%) |
| Decreased motor activity | 1 (6%) | 2 (15%) |
| Aggression | 1 (6%) | 1 (8%) |
| Akathisia | 1 (6%) | 0 (0%) |
| Head banging | 1 (7%) | 0 (0%) |
| Dizziness | 0 (0%) | 1 (8%) |
| Lethargy/tiredness | 0 (0%) | 1 (8%) |
| HEENT | | |
| Nasal congestion | 3 (18%) | 4 (31%) |
| Dry mouth | 1 (6%) | 3 (23%) |
| Blurred vision | 1 (6%) | 1 (8%) |
| Ear infection | 0 (0%) | 1 (8%) |
| Runny nose | 0 (0%) | 1 (8%) |
| Sore throat | 0 (0%) | 1 (8%) |
| Cold sore | 0 (0%) | 1 (8%) |
| Gastrointestinal | | |
| Decreased appetite | 4 (24%) | 5 (38%) |
| Nausea/vomiting | 2 (12%) | 2 (15%) |
| Constipation | 1 (6%) | 0 (0%) |
| Diarrhea | 0 (0%) | 1 (8%) |
| Renal | | |
| Increased urination | 1 (6%) | 1 (8%) |
| Bed wetting | 1 (6%) | 0 (0%) |
| Dermatological | | |
| Skin rash | 1 (6%) | 1 (8%) |
| Bug bite | 1 (6%) | 0 (0%) |
| Skin burn | 0 (0%) | 1 (8%) |

Abbreviations: DOTES, Dosage Record Treatment Emergent Symptom Scale; OAS, Overt Aggression Scale; arginine vasopressin (AVP); head, ears, eyes, nose, throat (HEENT). Adverse events are reported as counts and percentages. Fisher's Exact Test was used to test for differences in adverse events between the AVP and placebo treatment groups. No significant effects were discerned.

TABLE 5

Change from baseline in the safety assessments for the 4-week treatment trial

| Measure | Drug Treatment main effect | Change from baseline LSM +/− SE | |
|---|---|---|---|
| | | AVP | Placebo |
| Vital Sign | | | |
| BP, Systolic, Sitting (mmHg) | $F_{1,28} = 2.9584$; P = 0.0966 | 5.5 ± 2.53 | −1.1 ± 2.89 |
| BP, Diastolic, Sitting (mmHg) | $F_{1,28} = 2.5600$; P = 0.1200 | 3.2 ± 2.09 | −1.8 ± 2.39 |
| BP, Systolic, Standing (mmHg) | $F_{1,28} = 0.3844$; P = 0.5397 | 1.9 ± 2.38 | −0.3 ± 2.73 |
| BP, Diastolic, Standing (mmHg) | $F_{1,28} = 0.0289$; P = 0.8700 | 0.1 ± 2.31 | −0.5 ± 2.64 |
| BP Change Systolic (Standing-Sitting) | $F_{1,28} = 1.0816$; P = 0.3069 | −3.6 ± 2.76 | 0.8 ± 3.15 |
| BP Change Diastolic (Standin-Sitting) | $F_{1,28} = 1.2544$; P = 0.2726 | −3.1 ± 2.65 | 1.4 ± 3.03 |
| Pulse sitting (beats per minute) | $F_{1,28} = 0.8836$; P = 0.3563 | 1.9 ± 3.87 | 7.5 ± 4.43 |
| Pulse standing (beats per minute) | $F_{1,28} = 0.9604$; P = 0.3359 | 4.0 ± 3.57 | 9.3 ± 4.08 |
| Pulse change (beats per minute) | $F_{1,28} = 0.0025$; P = 0.9598 | 2.1 ± 2.75 | 1.8 ± 3.15 |
| Temperature (° F.) | $F_{1,28} = 2.3409$; P = 0.1369 | 0.2 ± 0.17 | −0.2 ± 0.19 |

TABLE 5-continued

Change from baseline in the safety assessments for the 4-week treatment trial

| Measure | Drug Treatment main effect | Change from baseline LSM +/− SE | |
|---|---|---|---|
| | | AVP | Placebo |
| Electrocardiogram | | | |
| Heart Rate (bpm) | $F_{1,26} = 0.4096; P = 0.5272$ | −2.5 ± 3.75 | 1.2 ± 4.32 |
| P Duration (ms) | $F_{1,25} = 0.2025; P = 0.6600$ | −2.6 ± 5.76 | 1.5 ± 6.95 |
| PR Intervals (ms) | $F_{1,26} = 0.3481; P = 0.5586$ | −4.6 ± 6.40 | 1.2 ± 7.39 |
| QRS Interval (ms) | $F_{1,26} = 0.3844; P = 0.5421$ | 0.4 ± 1.55 | 1.8 ± 1.78 |
| QT Interval (ms) | $F_{1,26} = 0.9604; P = 0.3378$ | 3.5 ± 5.53 | −4.8 ± 6.39 |
| Bazett's Corrected QT Interval (ms) | $F_{1,26} < 0.0001; P = 0.9979$ | −1.9 ± 5.07 | −1.9 ± 5.86 |
| Clinical Chemistry | | | |
| Sodium (mmol/L) | $F_{1,28} = 0.0081; P = 0.9328$ | 0.24 ± 0.63 | 0.15 ± 0.72 |
| Potassium (mmol/L) | $F_{1,28} = 0.2601; P = 0.6132$ | 0.15 ± 0.11 | 0.06 ± 0.13 |
| Chloride (mmol/L) | $F_{1,28} = 2.3716; P = 0.1348$ | 1.0 ± 0.56 | −0.31 ± 0.64 |
| $CO_2$ (mmol/L) | $F_{1,28} = 1.4400; P = 0.2395$ | −0.12 ± 0.57 | 0.92 ± 0.65 |
| Anion Gap (mmol/L) | $F_{1,28} = 0.0256; P = 0.8762$ | −0.65 ± 0.78 | −0.46 ± 0.89 |
| Glucose (mg/dL) | $F_{1,28} = 0.2704; P = 0.6099$ | 2.2 ± 4.41 | 5.7 ± 5.04 |
| Creatine (mg/dL) | $F_{1,28} = 1.2321; P = 0.2756$ | −0.017 ± 0.03 | 0.027 ± 0.03 |
| Urea Nitrogen (mg/dL) | $F_{1,28} = 2.4025; P = 0.1314$ | −1.3 ± 0.78 | 0.54 ± 0.89 |
| Calcium (mg/dL) | $F_{1,28} = 2.3716; P = 0.1355$ | 0.047 ± 0.07 | 0.20 ± 0.07 |
| Osmolality (Serum) (mOsm/kg) | $F_{1,28} = 2.6244; P = 0.1158$ | 0.18 ± 1.01 | −2.3 ± 1.15 |
| Osmolality (Urine) (mOsm/kg) | $F_{1,25} = 0.0625; P = 0.8027$ | 8.5 ± 82.6 | −23 ± 92.3 |
| Physiological | | | |
| Height (centimeters) | $F_{1,28} = 2.0736; P = 0.1619$ | 0.8 ± 0.23 | 0.3 ± 0.27 |
| Weight (kilometers) | $F_{1,28} = 0.0225; P = 0.8809$ | 0.3 ± 0.30 | 0.2 ± 0.34 |

Abbreviations: LSM, Least Square Mean; AVP, arginine vasopressin; BP, blood pressure. Within-subject changes from baseline were calculated for each measure, and the effect of treatment tested using a general linear model. No significant effects were discerned.

REFERENCES

1. A. P. Association, *Diagnostic and Statistical Manual of Mental Disorders* (Washington, DC, ed. 5th, 2013).
2. S. Webb, Drugmakers dance with autism. *Nature biotechnology* 28, 772-774 (2010).
3. H. E. Albers, The regulation of social recognition, social communication and aggression: vasopressin in the social behavior neural network. *Hormones and behavior* 61, 283-292 (2012).
4. I. F. Bielsky, S. B. Hu, K. L. Szegda, H. Westphal, L. J. Young, Profound impairment in social recognition and reduction in anxiety-like behavior in vasopressin V1a receptor knockout mice. *Neuropsychopharmacology: official publication of the American College of Neuropsychopharmacology* 29, 483-493 (2004).
5. M. J. Paul et al., Atypical Social Development in Vasopressin-Deficient Brattleboro Rats. *eNeuro* 3, (2016).
6. A. J. Guastella, A. R. Kenyon, G. A. Alvares, D. S. Carson, I. B. Hickie, Intranasal arginine vasopressin enhances the encoding of happy and angry faces in humans. *Biol Psychiatry* 67, 1220-1222 (2010).
7. A. J. Guastella, A. R. Kenyon, C. Unkelbach, G. A. Alvares, I. B. Hickie, Arginine Vasopressin selectively enhances recognition of sexual cues in male humans. *Psychoneuroendocrinology* 36, 294-297 (2011).
8. C. Brunnlieb et al., Vasopressin increases human risky cooperative behavior. *Proc Natl Acad Sci USA* 113, 2051-2056 (2016).
9. S. G. Tsikunov, S. G. Belokoskova, Psychophysiological analysis of the influence of vasopressin on speech in patients with post-stroke aphasias. *Span J Psychol* 10, 178-188 (2007).
10. F. Laczi et al., Effects of lysine-vasopressin and 1-deamino-8-D-arginine-vasopressin on memory in healthy individuals and diabetes insipidus patients. *Psychoneuroendocrinology* 7, 185-193 (1982).
11. J. Born et al., Sniffing neuropeptides: a transnasal approach to the human brain. *Nat Neurosci* 5, 514-516 (2002).
12. K. J. Parker et al., Arginine vasopressin in cerebrospinal fluid is a marker of sociality in nonhuman primates. *Science translational medicine*, (in press).
13. O. Oztan et al., Cerebrospinal fluid vasopressin and symptom severity in children with autism. under review, (under review).
14. J. T. Winslow, T. R. Insel, Neuroendocrine basis of social recognition. *Curr Opin Neurobiol* 14, 248-253 (2004).
15. L. J. Young, R. Nilsen, K. G. Waymire, G. R. MacGregor, T. R. Insel, Increased affiliative response to vasopressin in mice expressing the V1a receptor from a monogamous vole. *Nature* 400, 766-768 (1999).
16. K. J. Parker, T. M. Lee, Central vasopressin administration regulates the onset of facultative paternal behavior in *Microtus pennsylvanicus* (meadow voles). *Horm Behav* 39, 285-294 (2001).
17. Z. R. Donaldson, L. Spiegel, L. J. Young, Central vasopressin V1a receptor activation is independently necessary for both partner preference formation and expression in socially monogamous male prairie voles. *Behav Neurosci* 124, 159-163 (2010).
18. R. Landgraf et al., Viral vector-mediated gene transfer of the vole V1a vasopressin receptor in the rat septum: improved social discrimination and active social behaviour. *Eur J Neurosci* 18, 403-411 (2003).
19. S. M. Freeman, K. Inoue, A. L. Smith, M. M. Goodman, L. J. Young, The neuroanatomical distribution of oxytocin receptor binding and mRNA in the male rhesus macaque (*Macaca mulatta*). *Psychoneuroendocrinology* 45, 128-141 (2014).

20. J. T. Winslow, N. Hastings, C. S. Carter, C. R. Harbaugh, T. R. Insel, A role for central vasopressin in pair bonding in monogamous prairie voles. *Nature* 365, 545-548 (1993).
21. D. L. Christensen et al., Prevalence and Characteristics of Autism Spectrum Disorder Among Children Aged 8 Years—Autism and Developmental Disabilities Monitoring Network, 11 Sites, United States, 2012. *MMWR Surveill Summ* 65, 1-23 (2016).
22. D. S. Carson et al., Arginine Vasopressin Is a Blood-Based Biomarker of Social Functioning in Children with Autism. *PLoS One* 10, e0132224 (2015).
23. D. S. Carson et al., Plasma vasopressin concentrations positively predict cerebrospinal fluid vasopressin concentrations in human neonates. *Peptides* 61C, 12-16 (2014).
24. C. T. Wotjak et al., Dissociated central and peripheral release of vasopressin, but not oxytocin, in response to repeated swim stress: new insights into the secretory capacities of peptidergic neurons. *Neuroscience* 85, 1209-1222 (1998).
25. S. M. Kagerbauer et al., Plasma oxytocin and vasopressin do not predict neuropeptide concentrations in human cerebrospinal fluid. *J Neuroendocrinol* 25, 668-673 (2013).
26. K. J. Parker et al., Arginine vasopressin in cerebrospinal fluid is a marker of sociality in nonhuman primates. *Science translational medicine* 10, (2018).
27. M. Thibonnier, P. Coles, A. Thibonnier, M. Shoham, The basic and clinical pharmacology of nonpeptide vasopressin receptor antagonists. *Annu Rev Pharmacol Toxicol* 41, 175-202 (2001).
28. Z. V. Johnson, L. J. Young, Oxytocin and vasopressin neural networks: Implications for social behavioral diversity and translational neuroscience. *Neurosci Biobehav Rev* 76, 87-98(2017).
29. D. A. Baribeau, E. Anagnostou, Oxytocin and vasopressin: linking pituitary neuropeptides and their receptors to social neurocircuits. *Front Neurosci* 9, 335 (2015).
30. Y. Delville, K. M. Mansour, C. F. Ferris, Testosterone facilitates aggression by modulating vasopressin receptors in the hypothalamus. *Physiol Behav* 60, 25-29 (1996).
31. H. F. Zhang et al., Electro-acupuncture improves the social interaction behavior of rats. *Physiol Behav* 151, 485-493 (2015).
32. R. Zhang et al., Transcutaneous electrical acupoint stimulation in children with autism and its impact on plasma levels of arginine-vasopressin and oxytocin: a prospective single-blinded controlled study. *Research in developmental disabilities* 33, 1136-1146 (2012).
33. J. Vande Walle, M. Stockner, A. Raes, J. P. Norgaard, Desmopressin 30 years in clinical use: a safety review. *Curr Drug Saf* 2, 232-238 (2007).
34. J. Niemczyk, C. Wagner, A. von Gontard, Incontinence in autism spectrum disorder: a systematic review. *Eur Child Adolesc Psychiatry*, (2017).
35. P. S. Sorensen, H. Vilhardt, F. Gjerris, J. Warberg, Impermeability of the blood-cerebrospinal fluid barrier to 1-deamino-8-D-arginine-vasopressin (DDAVP) in patients with acquired, communicating hydrocephalus. *Eur J Clin Invest* 14, 435-439 (1984).
36. J. H. Robben, N. V. Knoers, P. M. Deen, Regulation of the vasopressin V2 receptor by vasopressin in polarized renal collecting duct cells. *Molecular biology of the cell* 15, 5693-5699 (2004).
37. H. Ratni et al., Discovery of highly selective brain-penetrant vasopressin 1a antagonists for the potential treatment of autism via a chemogenomic and scaffold hopping approach. *J Med Chem* 58, 2275-2289 (2015).
38. D. Umbricht et al., A Single Dose, Randomized, Controlled Proof-Of-Mechanism Study of a Novel Vasopressin 1a Receptor Antagonist (RG7713) in High-Functioning Adults with Autism Spectrum Disorder. *Neuropsychopharmacology* 42, 1924 (2017).
39. K. L. Gobrogge, Y. Liu, L. J. Young, Z. Wang, Anterior hypothalamic vasopressin regulates pair-bonding and drug-induced aggression in a monogamous rodent. *Proc Natl Acad Sci USA* 106, 19144-19149 (2009).
40. C. F. Ferris et al., Vasopressin/serotonin interactions in the anterior hypothalamus control aggressive behavior in golden hamsters. *J Neurosci* 17, 4331-4340 (1997).
41. R. Thompson, S. Gupta, K. Miller, S. Mills, S. Orr, The effects of vasopressin on human facial responses related to social communication. *Psychoneuroendocrinology* 29, 35-48 (2004).
42. V. Sclafani et al., Early Predictors of Impaired Social Functioning in Male Rhesus Macaques (*Macaca mulatta*). *PLoS One* 11, e0165401 (2016).
43. APA, *Diagnostic and Statistical Manual of Mental Disorders*. (American Psychiatric Association, Washington, DC, ed. 4th, Text Revision, 2000).
44. C. Lord, M. Rutter, A. Le Couteur, Autism Diagnostic Interview-Revised: a revised version of a diagnostic interview for caregivers of individuals with possible pervasive developmental disorders. *J Autism Dev Disord* 24, 659-685 (1994).
45. C. Lord et al., *Autism Diagnostic Observation Schedule, second edition* (ADOS-2) *manual (part* 1): *Modules* 1-4. (Western Psychological Services, Torrance, C A, 2012).
46. G. H. Roid, *Stanford Binet's Intelligence Scales, Fifth Edition, Technical Manual*, (Riverside Publishing, Itasca, IL, 2003).
47. W. Guy, Ed., *ECDEU Assessment Manual for Psychopharmacology*, (U. S. Department of Health, Education, and Welfare, Rockville, M D, 1976).
48. S. Baron-Cohen, S. Wheelwright, V. Scahill, J. Lawson, A. Spong, Are intuitive physics and intuitive psychology independent? A test with children with Asperger syndrome. *J Dev Learn Disord* 5, 47-78 (2001).
49. M. Korkman, U. Kirk, S. Kemp, *NEPSY-II Clinical and Interpretive Manual*, (Harcourt Assessment Inc., San Antonio, T X, 2007).
50. N. Tottenham et al., The NimStim set of facial expressions: judgments from untrained research participants. *Psychiatry Res* 168, 242-249 (2009).
51. C. A. Garvey, D. Gross, L. Freeman, Assessing psychotropic medication side effects among children. A reliability study. *J Child Adolesc Psychiatr Ment Health Nurs* 4, 127-131 (1991).
52. S. C. Yudofsky, J. M. Silver, W. Jackson, J. Endicott, D. Williams, The overt aggression scale for the objective rating of verbal and physical aggression. *American Journal of Psychiatry* 143, 35-39 (1986).
53. S. G. Gregory et al., Genomic and epigenetic evidence for oxytocin receptor deficiency in autism. *BMC Med* 7, 62 (2009).
54. S. S. Wang, W. Kamphuis, I. Huitinga, J. N. Zhou, D. F. Swaab, Gene expression analysis in the human hypothalamus in depression by laser microdissection and real-time PCR: the presence of multiple receptor imbalances. *Mol Psychiatry* 13, 786-799, 741 (2008).
55. A. C. Lossie et al., ENU mutagenesis reveals that Notchless homolog 1 (*Drosophila*) affects Cdkn1a and several members of the Wnt pathway during murine pre-implantation development. *BMC Genet* 13, 106 (2012).
56. J. N. Constantino et al., Validation of a brief quantitative measure of autistic traits: comparison of the social responsiveness scale with the autism diagnostic interview-revised. *J Autism Dev Disord* 33, 427-433 (2004).
57. J. N. Constantino et al., Validation of a brief quantitative measure of autistic traits: comparison of the social responsiveness scale with the autism diagnostic interview-revised. *J Autism Dev Disord* 33, 427-433 (2003).
58. C. J. Yatawara, S. L. Einfeld, I. B. Hickie, T. A. Davenport, A. J. Guastella, The effect of oxytocin nasal spray on social interaction deficits observed in young children with autism: a randomized clinical crossover trial. *Mol Psychiatry*, (2015).
59. M. G. Aman et al., Safety and Efficacy of Memantine in Children with Autism: Randomized, Placebo-Controlled Study and Open-Label Extension. *J Child Adolesc Psychopharmacol*, (2016).
60. K. J. Parker et al., Intranasal oxytocin treatment for social deficits and biomarkers of response in children with autism. *Proc Natl Acad Sci USA* 114, 8119-8124 (2017).
61. K. S. Lam, M. G. Aman, The Repetitive Behavior Scale-Revised: independent validation in individuals with autism spectrum disorders. *Journal of autism and developmental disorders* 37, 855-866 (2007).
62. S. Wigham, H. McConachie, Systematic review of the properties of tools used to measure outcomes in anxiety intervention studies for children with autism spectrum disorders. *PLoS One* 9, e85268 (2014).
63. S. W. White, D. Oswald, T. Ollendick, L. Scahill, Anxiety in children and adolescents with autism spectrum disorders. *Clin Psychol Rev* 29, 216-229 (2009).
64. P. A. Harris et al., Research electronic data capture (REDCap)-A metadata-driven methodology and workflow process for providing translational research informatics support. *J Biomed Inform* 42, 377-381 (2009).
65. A. Grafen, R. Hails, *Modern statistics for the life sciences*. (Oxford University Press, Oxford & New York, 2002), pp. xv, 351.

What is claimed is:

1. A method of treating autism spectrum disorder (ASD) in a subject, comprising:
   selecting for treatment a subject with pre-treatment blood arginine vasopressin levels greater than 1.0 pg/ml and greater than about 25% or more above the mean/normal pre-treatment arginine vasopressin blood levels of the treatment group of subjects, wherein the subject is 18 years of age or younger;
   administering to the selected subject an effective dose of intranasal arginine vasopressin (AVP),
   resulting in a decrease in at least one measure of social impairment, anxiety, or repetitive behaviors.

2. The method of claim 1, wherein the pre-treatment blood level of arginine vasopressin of the selected subject is ≥2.0 pg/ml.

3. The method of claim 1, wherein the pre-treatment blood level of arginine vasopressin of the selected subject is 1.456 pg/mL or more.

4. The method of claim 1, wherein the method treats social impairment.

5. The method of claim 1, wherein the subject is a child between 6 and 12 years of age.

6. The method of claim 1, wherein the subject is administered intranasal AVP between one and four times daily.

7. The method of claim 1, wherein the subject is administered up to 16 IU intranasal AVP between one and four times daily.

8. The method of claim 1, wherein the subject is between 6 and 9.5 years of age and is administered intranasal AVP at a dose of about 12 IU between one and four times daily.

* * * * *